US009913888B2

(12) United States Patent
Sørum

(10) Patent No.: US 9,913,888 B2
(45) Date of Patent: *Mar. 13, 2018

(54) FISH VACCINE

(71) Applicant: NORGES MILJØ-OG BIOVITENSKAPELIGE UNIVERSITET (NMBU), Ås (NO)

(72) Inventor: Henning Sørum, Oslo (NO)

(73) Assignee: NORGES MILJØ- OG BIOVITENSKAPELIGE UNIVERSITET (NMBU), Ås (NO)

( * ) Notice: Subject to any disclaimer, the term of this patent is extended or adjusted under 35 U.S.C. 154(b) by 0 days.

This patent is subject to a terminal disclaimer.

(21) Appl. No.: 15/036,229

(22) PCT Filed: Nov. 13, 2014

(86) PCT No.: PCT/EP2014/074482
§ 371 (c)(1),
(2) Date: May 12, 2016

(87) PCT Pub. No.: WO2015/074943
PCT Pub. Date: May 28, 2015

(65) Prior Publication Data
US 2016/0296615 A1    Oct. 13, 2016

(30) Foreign Application Priority Data

Nov. 13, 2013 (NO) .................................. 20131511

(51) Int. Cl.
| A61K 39/02 | (2006.01) |
| A61K 39/00 | (2006.01) |
| A23K 10/16 | (2016.01) |
| A23K 10/18 | (2016.01) |
| A23K 50/80 | (2016.01) |
| C12N 1/20 | (2006.01) |
| C12R 1/01 | (2006.01) |

(52) U.S. Cl.
CPC .......... *A61K 39/0216* (2013.01); *A23K 10/16* (2016.05); *A23K 10/18* (2016.05); *A23K 50/80* (2016.05); *A61K 39/0208* (2013.01); *A61K 39/105* (2013.01); *C12N 1/20* (2013.01); *C12R 1/01* (2013.01); *A61K 2039/521* (2013.01); *A61K 2039/522* (2013.01); *A61K 2039/54* (2013.01); *A61K 2039/552* (2013.01); *A61K 2039/70* (2013.01)

(58) Field of Classification Search
CPC ........ A61K 2039/521; A61K 2039/552; A61K 39/0208; A61K 39/0216; A61K 2039/54; A61K 2039/70; A61K 39/02; A61K 39/107; A61K 39/116; A61K 2039/522; A61K 39/105; C12N 1/20; C12R 1/01; A23K 10/16; A23K 10/18
See application file for complete search history.

(56) References Cited

U.S. PATENT DOCUMENTS

| 3,492,400 A | 1/1970 | Klontz et al. |
| 3,862,313 A | 1/1975 | Fryer et al. |
| 2016/0296614 A1 | 10/2016 | Sørum et al. |
| 2016/0296615 A1 | 10/2016 | Sørum et al. |

FOREIGN PATENT DOCUMENTS

| EP | 0640348 A1 | 3/1995 |
| WO | 2012162496 A1 | 11/2012 |
| WO | 2013171236 A1 | 11/2013 |
| WO | 2015074943 A1 | 5/2015 |
| WO | 2015074946 A1 | 5/2015 |

OTHER PUBLICATIONS

Ruma Guidelines. Responsible use of vaccines and vaccination in fish production. pp. 1-24, Nov. 2006.*
Illustrated Stedman's Medical Dictionary, 24th Edition, Williams & Wilkins, Baltimore, p. 707, 1982.*
Webster's II New Riverside University Dictionary, The Riverside Publishing Company, p. 933, 1984.*
Rijal et al. Water Sci. Technol. 43: 155-162, 2001, abstract.*
International Search Report/Written Opinion dated Apr. 8, 2015, of related International Application No. PCT/EP2014/074491, Filed Nov. 13, 2014. 13 Pages.
International Search Report/Written Opinion dated Feb. 2, 2015, of corresponding International Application No. PCT/EP2014/074482, Filed Nov. 13, 2014. 12 Pages.
Norwegian ITS Report dated Feb. 5, 2014, of Priority application NO20131511 filed Nov. 13, 2013. 4 pages.
Norwegian Search Report dated Apr. 12, 2014, of Priority application NO20131511 filed Nov. 13, 2013. 2 pages.
Norwegian Search Report dated Apr. 14, 2014, of Priority application NO20131512 filed Nov. 13, 2013. 2 pages.
Norwegian ITS Report dated Feb. 5, 2014, of Priority application NO20131512 filed Nov. 13, 2013. 4 pages.
Austin "Developments in vaccination against fish bacterial disease" 2012, Woodhead Publishing Limited 2012, Food science technology and nutritions 218-243.
Beaz-Hidalgo et al., "*Aliivibrio finisterrensis* sp. nov., isolated from Manila clam, Ruditapes philippinarum and emended description of the genus Aliivbrio." Int J Syst Evol Microbiol. Jan. 2010;60(Pt 1): 223-8.
Benediktsdottir et al., "Characterization of Vibrio viscosus and Vibrio wodanis isolated at different geographical locations: a proposal for reclassification of Vibrio viscosus as Moritella viscosa comb. nov." Int J Syst Evol Microbiol. Mar. 2000;50 Pt 2:479-88.
Bercovich et al., "*Bizionia argentinensis* sp. nov., isolated from surface marine water in Antarctica." Int J Syst Evol Microbiol. Oct. 2008;58(Pt 10):2363-7.
Bjornsdottir et al., "Identification of type VI secretion systems in Moritella viscosa" Veterinary Microbiology 158 (2012) 436-442.
Bowman et al., "Novel members of the family Flavobacteriaceae from Antarctic maritime habitats including *Subsaximicrobium wynnwilliamsii* gen. nov., sp. nov., *Subsaximicrobium saxinquilinus* sp. nov., *Subsaxibacter broadyi* gen. nov., sp. nov., *Lacinutrix copepodicola* gen. nov., sp. nov., and novel species of the genera Bizionia, Gelidibacter and Gillisia." Int J Syst Evol Microbiol. Jul. 2005;55(Pt 4):1471-86.

(Continued)

*Primary Examiner* — S. Devi
(74) *Attorney, Agent, or Firm* — Casimir Jones, S.C.

(57) ABSTRACT

The present document discloses a new species of *Bizionia*, herein denoted *Bizionia piscinecroseptica* and a reference strain of this bacterium denoted *Bizionia* sp. 130524K2F7 which has been deposited at the National Collection of Industrial and Marine Bacteria and has been assigned accession number NCIMB 42183. Further disclosed is the medical use of bacteria of the genus *Bizionia* for vaccinating fish against a new disease identified and herein denoted bizioniosis.

11 Claims, 49 Drawing Sheets

(56) References Cited

OTHER PUBLICATIONS

Bruno et al., "Vibrio viscosus in farmed Atlantic salmon *Salmo salar* in Scotland: field and experimental observations" Dis Aquat Org, 1998, vol. 34: 161-166.

Cipriano et al., "Flavobacterium psychophilum, cause of Bacterial Cold-Water Disease and Rainbow Trout Fry Syndrome" 2005, Fish Disease Leaflet No. 86, 44 pages.

Dixon et al., "Vaccines for finfish aquaculture: What do we need to know to make them work?" Electronic Journal of Biotechnology, vol. 15, No. 5 (2012). 10 pages.

Gudmundsdottir et al., "Vaccination against atypical furunculosis and winter ulcer disease of fish." Vaccine. Jul. 26, 2007;25(30):5512-23.

Handlinger et al., "The pathology of Flexibacter maritimus in aquaculture species in Tasmania, Australia" Journal of Fish Diseases 1997, 20, 159-168.

Hastein et al., "Bacterial vaccines for fish—an update of the current situation worldwide." Dev Biol (Basel). 2005;121:55-74.

Izumi et al., "Relationship between gyrA Mutations and Quinolone Resistance in Flavobacterium psychrophilum Isolates" Applied and Environmental Microbiology, Jul. 2004, p. 3968-3972.

<Karlsen et al., "Moritella viscosa bypasses Atlantic salmon epidermal keratocyte clearing activity and might use skin surfaces as a port of infection" Veter. Mikrobiol. 154: 353-362, 2012.

Løvoll et I., "Atlantic salmon bath challenged with Moritella viscosa—Pathogen invasion and host response" 2009, Fish Shellfish Immunol, 26: 877-884.

Lunder et al., "'Winter ulcer' in the Atlantic salmon *Salmo salar*. Pathological and bacteriological investigations and transmission experiments" Dis aquat Org, 1995, vol. 23: 39-49.

Nedashkovskaya et al., "*Bizionia paragorgiae* gen. nov., sp. nov., a novel member of the family Flavobacteriaceae isolated from the soft coral *Paragorgia arborea*." Int J Syst Evol Microbiol. Jan. 2005;55(Pt 1):375-8.

Nematollahi et al., "Flavobacterium psychrophilum infections in salmonid fish" Journal of Fish Diseases 2003, 26, 563-574.

Norwegian Veterinary Institute—Fish Health Report 2012 "The Health Situation in Norwegian Aquaculture 2012" Aug. 12, 2013. 38 Pages.

Prasad et al., "Diversity and Bioprospective Potential (Cold-Active Enzymes) of Cultivable Marine Bacteria from the Subarctic Glacial Fjord, Kongstjorden" Curr Microbiol (2014) 68:233-238.

Toranzo et al., "A review of the main bacterial fish diseases in mariculture systems" Aquaculture 246 (2005) 37-61.

Torella et al., "Microcultural Study of Bacterial Size Changes and Microcolony and Ultramicrocolony Formation by Heterotrophic Bacteria in Seawatert" Appl Environ Microbiol. Feb. 1981;41(2):518-27.

Whitman et al. "Isolation and Characterization of a New Vibrio Spp. (*Vibrio wodanis*) Associated with 'Winter Ulcer Disease' in Sea Water Raised Atlantic Salmon (*Salmo salar* 1.) in New Brunswick." Ed. C. I. Hendry & S. E. McGladdery. Moncton, NB: Aquaculture Association of Canada, St. Andrews, NB, 2001. 115-117. Print. Aquaculture Canada 2000., St. Andrews, NB.

* cited by examiner

FISH VACCINE

CROSS REFERENCE TO RELATED APPLICATIONS

The present application is a Section 371 U.S. national stage entry of pending International Patent Application No. PCT/EP2014/074482, international filing date Nov. 13, 2014, which claims priority to NO Patent Application No. 20131511, filed Nov. 13, 2013, the contents of which are incorporated by reference in their entireties.

FIELD OF INVENTION

The present disclosure relates to the field of vaccines, particularly vaccines for vaccinating fish against disease.

BACKGROUND

Winter ulcer is a known and only partly solved problem within the salmonid farming industry, especially relevant for the Atlantic salmon and rainbow trout farming. Winter ulcer causes annual losses of around NOK 100 million to the Norwegian aquaculture industry. In addition new findings show that more than 7 million salmons already vaccinated against winter ulcer are potentially lost to the industry only during the first 3 months after sea transfer due to ulcers that often is demonstrated to be winter ulcer. Industry officials have also identified a substantial lack of reporting of the illness, as the reporting of this disease is not mandatory. Out of the NOK 100 million registered losses, NOK 20 million are caused by down-classification of fish products due to scars and damaged muscle tissue which again causes a lowered meat quality.

Winter ulcer has also been a problem to the aquaculture industry in Scotland, Iceland, Faroe Islands, Ireland, Canada and Maine in USA (Bruno et al. 1998, Gudmundsdottir et al. 2006, Whitman et al. 2000).

*Moritella viscosa* (previously called *Vibrio viscosus*) has since long been shown to cause winter ulcer in farmed salmonid fish. From the first known outbreaks of disease in the 1980s focus has been on preventing and controlling the disease by controlling the bacterium *M. viscosa*. Since 1993, fish have been vaccinated against winter ulcer, and the main strategy today is to use a multi-component vaccine in vaccination of smolts before sea launch. *M. viscosa* is one of the up to six microbial components in the multi-component vaccines from all the vaccine producers. Other components besides *M. viscosa* are intended to protect against other diseases than winter ulcer. Vaccination of farmed Atlantic salmon has for nearly three decades been performed with one single intra-peritoneal injection of a multi-component vaccine protecting against up to 6 different infectious diseases before smoltification and sea launch. Since vaccination against winter ulcer started the vaccine effect has not been optimal, being successful with ≥60% relative protection.

Aunsmo et al. in 2008 document ulcers as accounting for 43% of the mortality in Atlantic salmon smolts already vaccinated against winter ulcer during the 3 first months after transfer to sea. It was shown that ulcers occurred in outbreaks with both *M. viscosa* and *V. wodanis* isolated from the kidneys of vaccinated but diseased salmon. In addition ulcers occurred as a cause of low baseline mortality during the first 3 months. Further winter ulcer occurs as a problem in all parts of the growth period.

The diseased post-smolts will also have a lower chance of becoming fully grown salmons having a higher mortality rate. The study published by Arnfinn Aunsmo in his 2009 Ph.D. thesis, entitled "Health related losses in sea farmed Atlantic salmon-quantification, risk factors and economic impact", at the Norwegian School of Veterinary Science (ISBN 978-82-7725-168-4, h.) (Aunsmo et al. (2008) had followed 2.7 million vaccinated post-smolts after transfer to sea in 20 different cages at 10 different localities in Norway. Overall mortality of the smolts was about 2.5% with the main cause of mortality explained by wounds (mainly winter ulcer) accounting for 43% of deaths in spite of the use of the only relatively effective commercial multi-component vaccine with the winter ulcer component. Extrapolated, 2.5% of the about 280 millions of salmon smolts 'launched' in total annually in Norway die from wounds that primarily are caused by winter ulcer the first 3 months after transfer from freshwater to net pens in sea.

Winter ulcer occurs throughout the complete growth period except for the summer months and the total losses including loss of salmon near to slaughter is not known. However, in 2008 it was reported a direct loss from down-classification of slaughtered salmon of NOK 20 million suspected to be mainly caused by winter ulcer in only one single salmon farm (ref Fiskehelserapporten VI, 2008).

Winter ulcer is a disease not mandatory to report, but by an annual phone call to the local Fish Health Services made by an official at the National Veterinary Institute annually between 35 and 55 farms are "remembered" to have had outbreaks of winter ulcer by the various Fish Health Services. In the fish health report from the National Veterinary Institute covering 2010 it is noted that a "Smolt syndrome" has been recorded just after transfer to sea. The smolts grow poorly and develop ulcers and it is related to improper smoltification in large batches of salmon transferred to unusually cold water. It is reason to believe that winter ulcer bacteria together with *Tenacibaculum* spp. bacteria may be related to these ulcer problems.

In summary, there is a need in the art to overcome or at least mitigate the problems associated with disease in fish, such as *Salmonidae*, by finding alternative vaccine solutions to the vaccines available as of today. There is a further need in the art for improvements of the vaccines to winter ulcer. There is a further need in the art for an improved vaccine which will reduce the loss caused by ulcers in the salmonid farming and also improve the product quality due to the occurrence of reduced scars and connective tissue in the meat of salmon surviving winter ulcer especially in spring and summer when sea water temperatures rise and ulcers heal leaving scars.

SUMMARY

The above problems have now been mitigated or overcome by the finding that a genus of bacteria which has previously not been considered to be pathogenic indeed is involved in causing disease in fish.

The present document is therefore directed to a composition comprising *Bizionia* sp. and/or an antigen thereof for use as a medicament. Said *Bizionia* sp. may e.g. be selected from the group consisting of *Bizionia saleffrena*, *Bizionia gelidisalsuginis*, *Bizionia paragorgiae*, *Bizionia myxarmorum*, *Bizionia algoritergicola* and *Bizionia piscinecroseptica*. The *Bizionia* sp. may also be *Bizionia piscinecroseptica*, such as *Bizionia* sp. 130524K2F7, which has been deposited at National Collection of Industrial and Marine Bacteria and has been assigned accession number NCIMB 42183 (for details regarding the deposit, see elsewhere herein). When bacterial cells are present in the composition these may be inactivated. An exemplary antigen but bacterial cells is an extracellular product, such as a supernatant comprising used growth medium. The composition may further comprise a pharmaceutically acceptable excipient and/or adjuvant. The composition may further comprise bacteria of other genera and/or species and/or strains and/or an antigen of such bacteria. Examples of such bacteria of other genera and/or species and/or strains may be selected from the group consisting of *Bizionia* sp, *Bizionia piscinecroseptica Moritella viscosa, Aliivibrio wodanis, Tenacibaculum* sp, *Tenacibaculum maritimum, Vibrio* sp, *Photobacter* sp, *Aeromonas salmonicida* ss *salmonicida, Aliivibrio logei, Aliivibrio salmonicida, Flavobacterium, Flavobacterium psychrophilum, Flavobacterium columnare, Aliivibrio friggiae* and/or *Vibrio anguillarum*, but are not limited thereto. The composition may further comprise *Aliivibrio friggiae*, and/or an antigen(s) thereof. The composition may further comprise *Aliivibrio wodanis* and/or an antigen(s) thereof. The composition may further comprise *Aliivibrio wodanis*, and/or an antigen(s) thereof, and *Aliivibrio friggiae*, and/or an antigen(s) thereof. The composition may further comprise *Moritella viscosa*. The composition may be a vaccine composition. The present document is also directed to a composition as disclosed herein as such.

The present document is also directed to a method for preparing a composition as defined herein, said method comprising the steps of:
  a) cultivating bacteria of *Bizionia* sp. alone or in combination with other bacteria;
  b) optionally separating said bacteria from their growth medium;
  c) inactivating said bacteria;
  d) optionally mixing said bacteria with a pharmaceutically acceptable excipient and/or adjuvant.

In such a method the bacteria of *Bizionia* sp. may be cultivated together with one or more bacterium selected from the group consisting of another *Bizionia* sp, *Bizionia piscinecroseptica, Moritella viscosa, Aliivibrio wodanis, Tenacibaculum* sp, *Tenacibaculum maritimum, Vibrio* sp, *Photobacter* sp, *Aeromonas salmonicida* ss *salmonicida, Aliivibrio logei, Aliivibrio salmonicida, Flavobacterium, Flavobacterium psychrophilum, Flavobacterium columnare, Aliivibrio friggiae* and/or *Vibrio anguillarum*. Formalin or heat may be used for inactivating the bacteria. In a method for preparing a composition according to the present document formalin and/or heat may be used for inactivating the bacteria. Alternatively, or in addition, the bacteria may be inactivated by attenuating said bacteria. The present document is also directed to a composition obtainable by the method disclosed herein.

The present document is also directed to a composition comprising as defined herein for medical use. The present document is also directed to a composition as defined herein for use as a vaccine.

The present document is also directed to a composition comprising *Bizionia* sp. and/or an antigen thereof as defined herein for use for the treatment and/or prevention of bizioniosis. The composition may be administered by intraperitoneal injection, bath vaccination and/or by oral vaccination.

The present document is also directed to the use of *Bizionia* sp. and/or an antigen thereof as defined herein or a composition as defined herein for the manufacture of a medicament for the treatment and/or prevention of bizioniosis. The medicament may be administered by intraperitoneal injection, bath vaccination and/or by oral vaccination.

The present document is also directed to a method for treating and/or preventing bizioniosis comprising the administration of a pharmaceutically effective amount of composition as defined herein to a subject in need thereof. The administration may be performed by intraperitoneal injection, bath vaccination and/or by oral vaccination.

The present document is also directed to an isolated and biologically pure strain of a bacterium of the species *Bizionia piscinecroseptica*. The present document is further directed to a biologically pure strain of *Bizionia* sp. 130524K2F7, which has been deposited at the National Collection of Industrial, Food and Marine Bacteria and has been assigned accession number NCIMB 42183.

The present document is also directed to a kit for vaccinating fish comprising a composition as defined herein, means for handling said composition and optionally instructions for use.

Other features and advantages of the invention will be apparent from the following detailed description, drawings, examples, and from the claims.

The IInd generation vaccine was identical to the IIIrd generation vaccine except that the adjuvant was 100% FICA.

The Ist generation vaccine was identical to the IIIrd and IInd generation vaccines except that no adjuvant was added.

The commercial vaccine was purchased through a detail seller from a commercial batch of vaccine produced in 2012 by a vaccine company with a substantial market share.

On the 21 Dec. 2012 the complete tank population of Atlantic salmon was challenged by immersion in sea water with a culture of *Aliivibrio friggiae* for one hour and on the 23. January to the beginning of June 2013 there was a chronic outbreak of friggiosis in the tank with approximately a similar mortality rate in the groups except for Ist generation vaccine that had no adjuvant that lost more of its protectivity towards the end of the experiment compared to the adjuvanted vaccines. In the three parallel tanks of the vaccination experiment there were only single cases of friggiosis with a lower frequency than in the challenged tank.

In August and September-12 there was a heavy outbreak of tail- and fin rot with septicemia in the tank.

Figure 44:
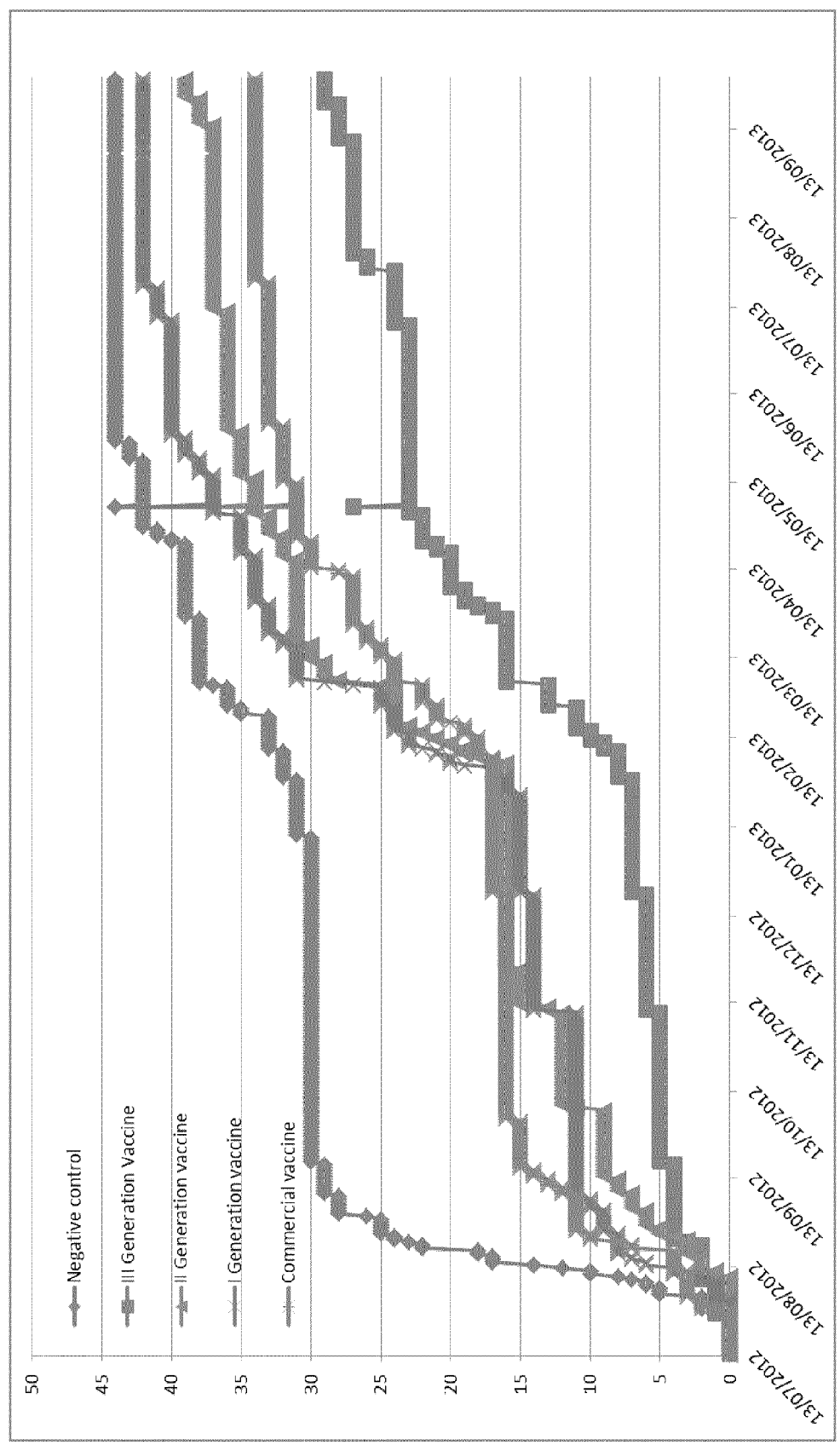
FIG. 44: Atlantic salmon challenged in a vaccination experiment with natural seawater from 13. Jul. 2012 to the end of October 2013. Fifty smolts were placed in each of the five experimental groups. Negative control smolts were vaccinated intraperitoneally (ip) with phosphate buffered saline (PBS). The IIIrd generation vaccine contained antigens from *Moritella viscosa* and *Aliivibrio wodanis* in various culture conditions in single and mixed cultures with high (2.5%) and low (0.9%) NaCl in the media and with incubation under high (10° C.) and low (8° C.) temperature. In addition *Aliivibrio salmonicida*, *Vibrio anguillarum* and *Aeromonas salmonicida* subspecies *salmonicida* included as inactivated antigens in the vaccine. The adjuvant added the vaccine was a mixture of glucan (60%) and Freunds incomplete adjuvant (FICA) (40%).
Figure 45:
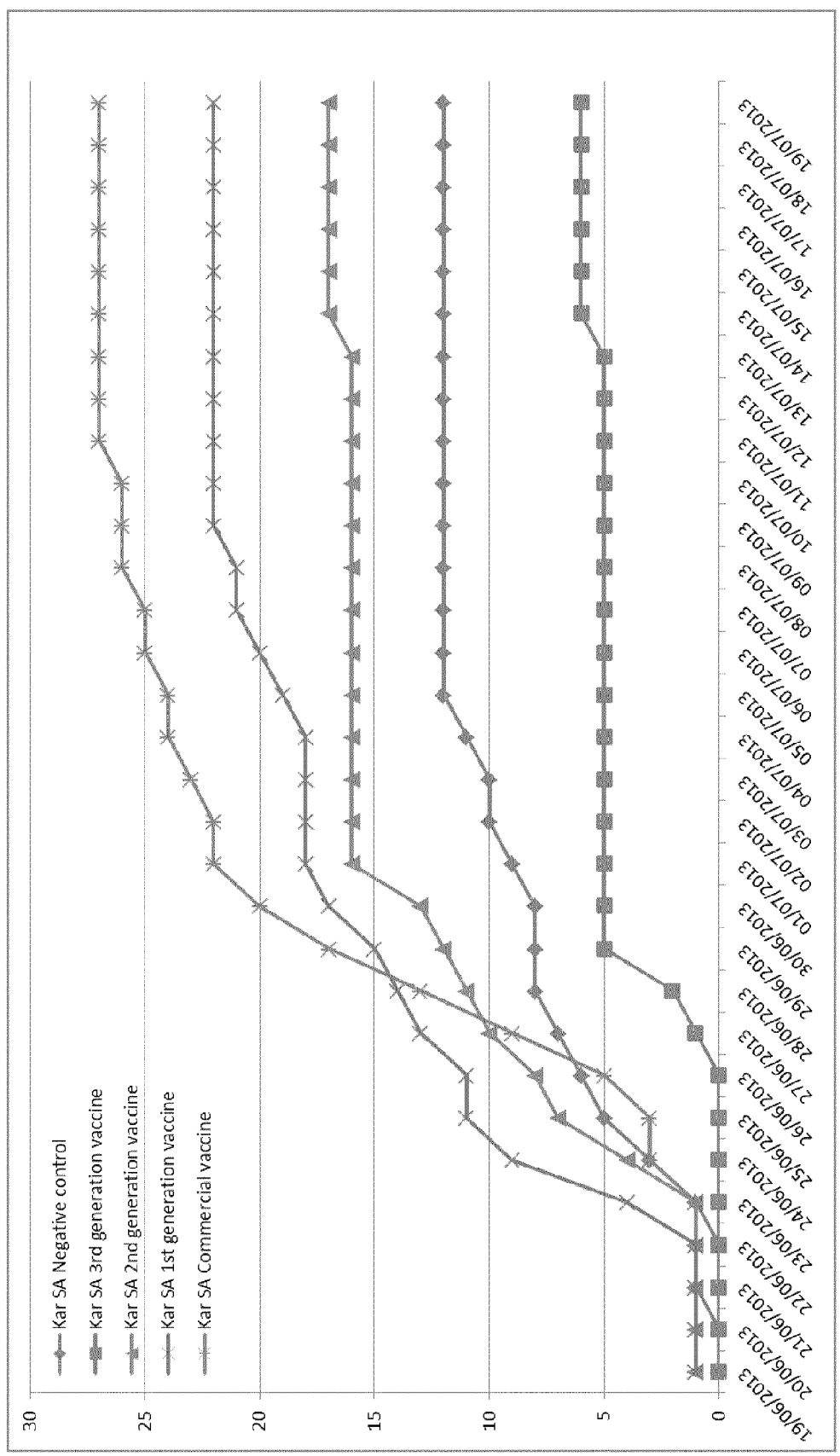
Figure 46:
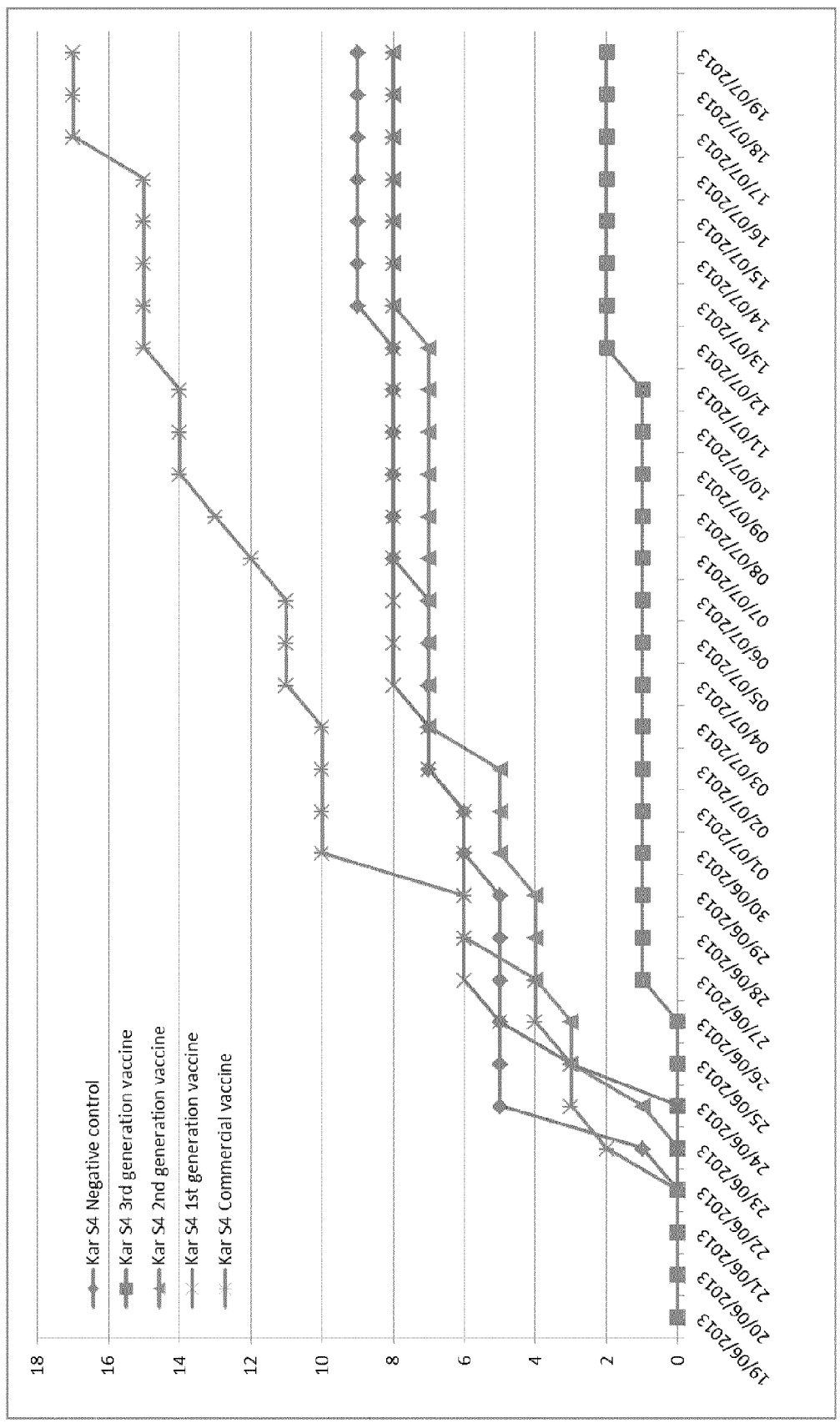
Figure 47:
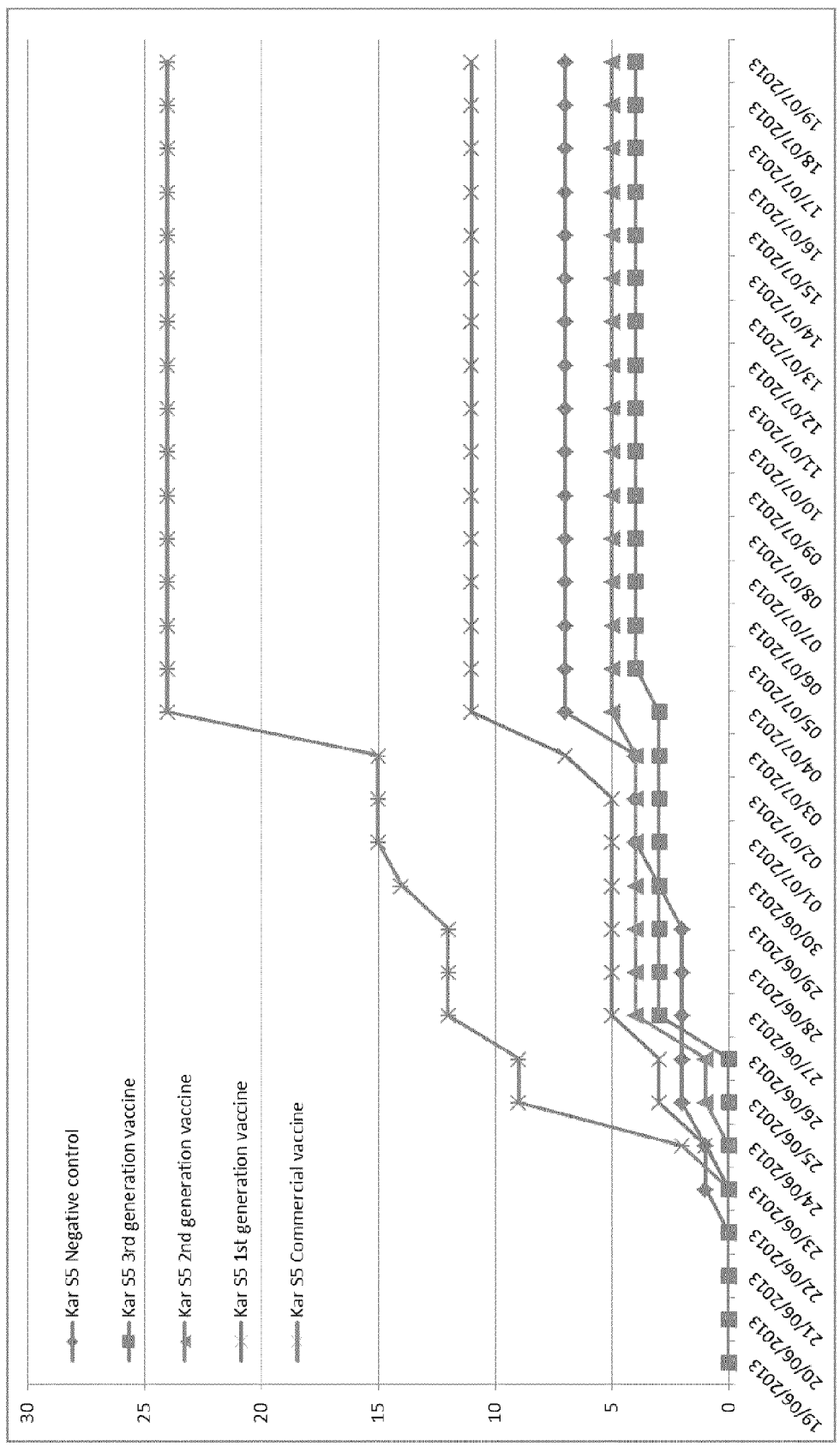

FIGS. 45, 46 and 47: A vaccination experiment in the identical tanks "Kar SA", "Kar S4 and "Kar S5" stocked with Atlantic salmon from the same population was challenged identically with natural seawater from 19 Jun. 2013 to the end of October 2013. Fifty smolts were placed in each of the five experimental groups of the tanks. Negative control smolts were vaccinated intraperitoneally (ip) with phosphate buffered saline (PBS). The IIIrd generation vaccine contained antigens from *Moritella viscosa* and *Aliivibrio wodanis* in various culture conditions in single and mixed cultures with high (2.5%) and low (0.9%) NaCl in the media and with incubation under high (10° C.) and low (8° C.) temperature. *Aliivibrio friggiae* (strain 130206K7F2506) and *Aliivibrio wodanis* in various culture conditions in single and mixed cultures with high (2.5%) and low (0.9%) NaCl in the media and with incubation under high (10° C.) and low (8° C.) temperature were added to the vaccine. *Vibrio splendidus* incubated at 8° C. in high (2.5%) NaCl was added. Three strain variants og *V. logei* cultivated in low (8° C.) temperature in high (2.5%) and low (0.9%) NaCl were added as antigens. Two *Moritella* sp. of uncharacterized species were incubated at 8° C. in high (2.5%) NaCl. *Vibrio tapetis* was also added after cultivation at 8° C. in high (2.5%) NaCl. A culture of *Bizionia piscinecroseptica* species novo was cultivated at 10° C. in high (2.5%) NaCl. In addition *Aliivibrio salmonicida*, *Vibrio anguillarum* and *Aeromonas salmonicida* subspecies *salmonicida* was included as inactivated antigens in the vaccine. The adjuvant added the vaccine was a mixture of glucan (60%) and Freunds incomplete adjuvant (FICA) (40%). The IInd generation vaccine was identical to the IIIrd generation vaccine except that the antigens of *Bizionia piscinecroseptica* species novo were deleted. The Ist generation vaccine was the same as the IIrd generation vaccine in FIG. 44 with the *M. viscosa* and *A. wodanis* antigens from various culture condition added to the antigens of *V. anguillarum*, *Aliivibrio salmonicida* and *Aeromonas salmonicida* subspecies *salmonicida*. The commercial vaccine was purchased through a detail seller from a commercial batch of vaccine produced in 2012 by a vaccine company with a substantial market share.

Figure 48:
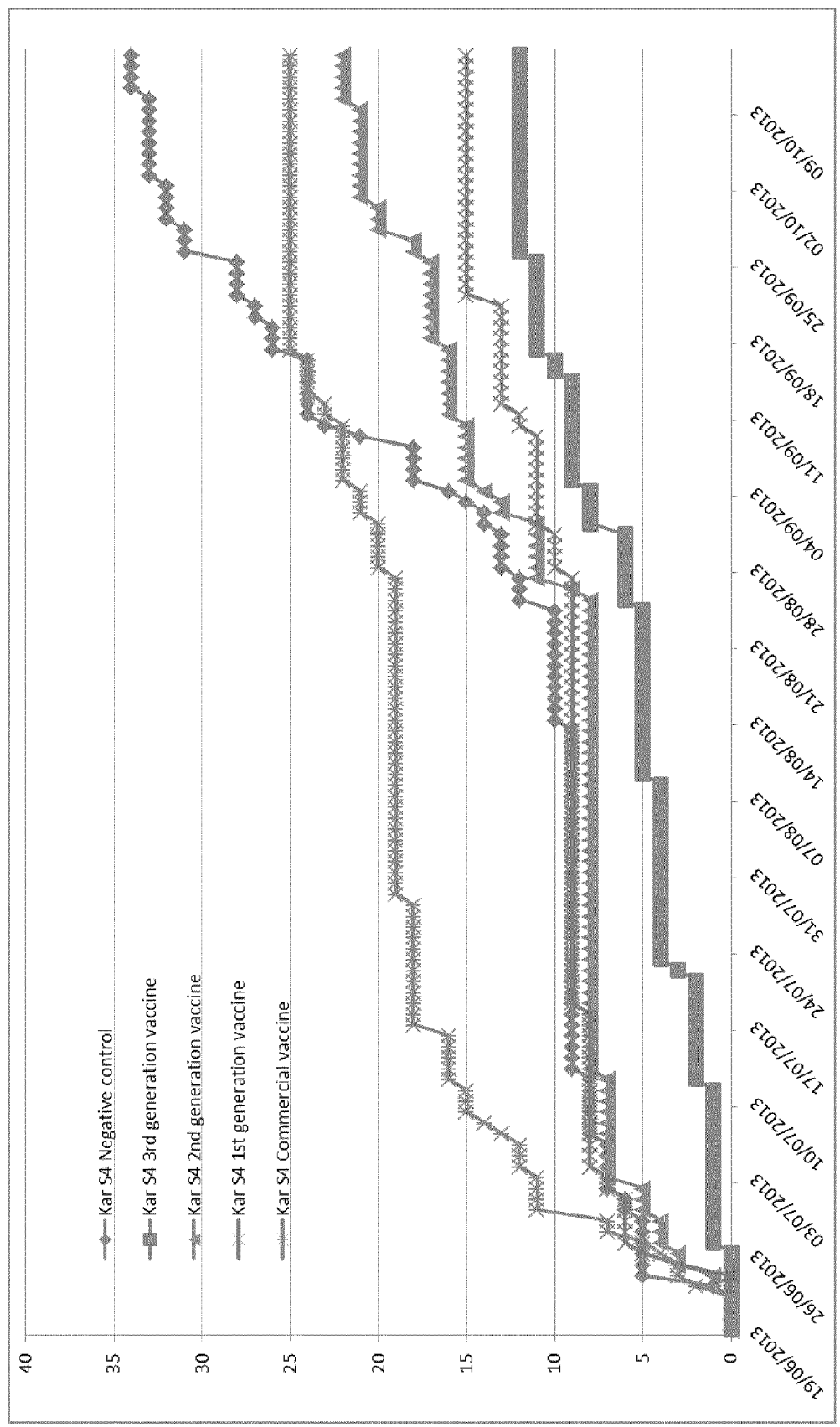

FIG. 48: The tank "Kar S4" (see FIG. 45) was monitored during addition of brackish water (2% salt) from 7 August to 16 August to reduce mortality. From 16 August full sea water was added and the tank was monitored with natural sea water challenge through mid-October.

Figure 49:
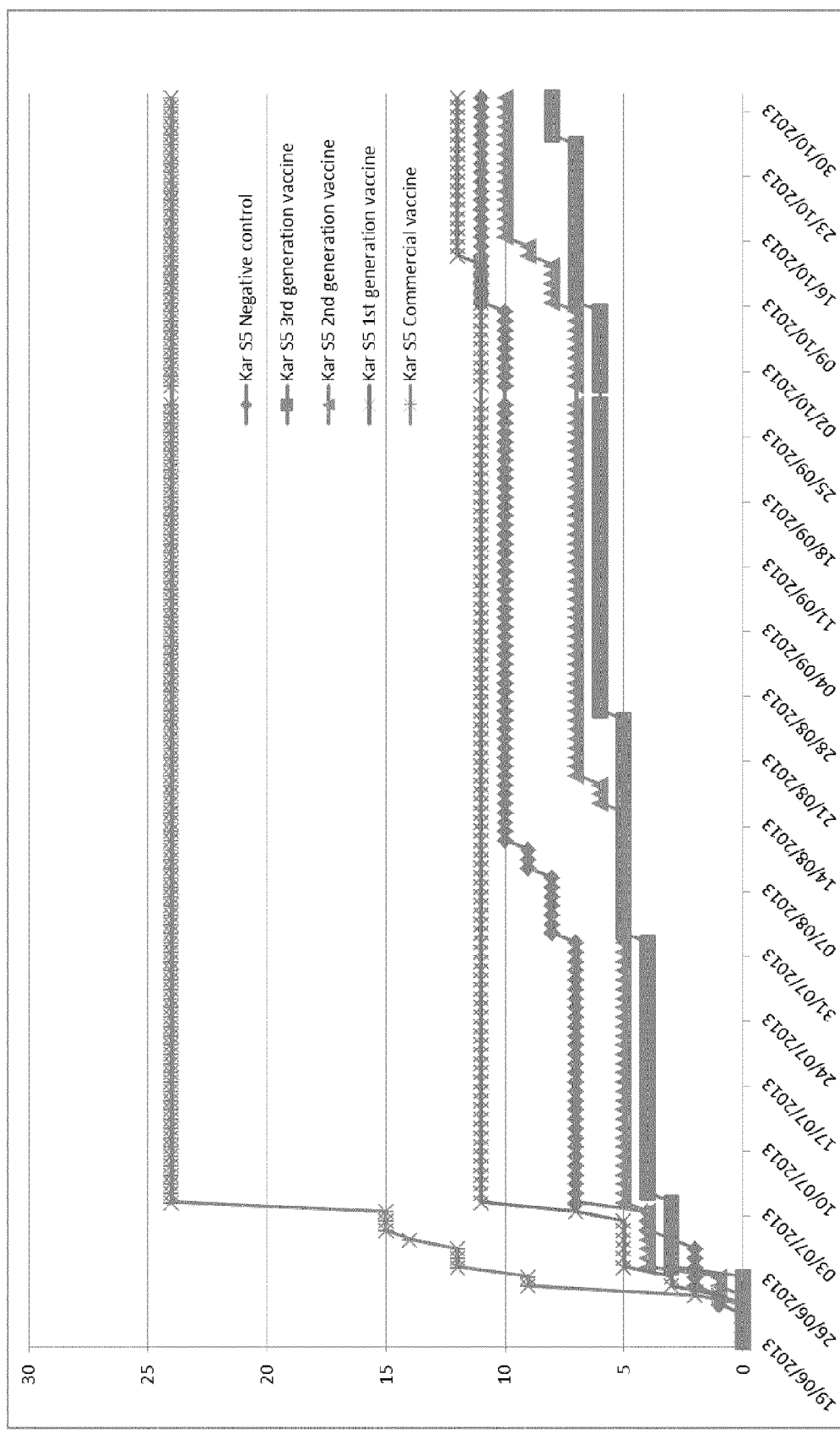

FIG. 49: The tank "Kar S5" (see FIG. 476) was monitored during addition of brackish water (2% salt) from 7 Aug. to 8 Oct. 2013 to reduce mortality. From 8. October full sea water was added and the tank was monitored with natural sea water challenge through the end of October.

DEFINITIONS

"Winter ulcer" is a disease which is characterized by skin ulcers that develop from skin swellings into open ulcers and later into larger ulcerated skin areas where the underlying muscle tissue is exposed and often destroyed by necrosis. Winter ulcer is mainly occurring at sea water temperatures from <6 to 8° C. At these temperatures *M. viscosa* is most clinically active and aggressively attacks the skin of the fish directly creating small ulcers as well as infect the fish septicemically mainly through the gill epithelium (Lunder et al. 1995, Løvoll et al. 2009, Karlsen et al. 2012).

"*Salmonidae*" is a family of ray-finned fish, which is the only living family currently placed in the order Salmoniformes. These are also referred to herein as salmonids. *Salmonidae* includes salmon, trout, chars, freshwater whitefishes and graylings.

A "culture" includes all forms of culture, both in broth, on agar and in any other media like eukaryotic cell cultures, eukaryotic/animal/fish tissue within research animals or any other physical measure. A "single culture" refers to a culture containing only one bacterial strain, i.e. a pure culture. A "mixed culture" refers to a culture wherein two or more bacterial strains, species and/or general are grown together. In such a mixed culture, the growth of a bacterium in the presence of at least one bacterium of another strain, species and/or genera may affect the bacteria's antigenic presentation. The temperature and the salt concentration (e.g. NaCl) conditions for each culture can be determined separately, depending on the circumstances and the materials used.

An "adjuvant" is a pharmacological or immunological agent that modifies the effect of other agents, such as a drug or vaccine. An adjuvant may be included in a composition as defined herein to enhance the recipient's immune response to a supplied vaccine, while keeping the injected foreign material to a minimum. Examples of adjuvants are oil emulsions, such as Freunds Incomplete, and aluminum salts.

A "vaccine" as referred to herein, may refer to a prophylactic and/or a therapeutic vaccine. A "vaccine", which is a term well-known in the art, is a biological preparation that improves immunity to a particular disease. Usually, a vaccine contains an agent that resembles a disease-causing microorganism, and is often made from weakened or killed forms of the microbe, its toxins or one or more of its surface proteins. The agent stimulates the body's immune system to recognize the agent as foreign, destroy it, and "remember" it, so that the immune system can more easily recognize and destroy any of these microorganisms during later encounters. The agent that provides the immunizing effect may be called an antigen. In the context of the present document, an antigen may be a bacterial cell(s), a bacterial extracellular product, a protein or part thereof or another bacterially produced substance/component.

The term "inactivated bacteria" refers to bacteria which due to one or more modifications have lost their virulence, but which still are able to induce an immune response in a recipient, e.g. a fish, which is sufficient to provide an immunizing effect. A component or an antigenic part of a bacterium, such as a surface protein or a part thereof, is a component or part of a bacterium which by itself is sufficient to induce an immune response. As disclosed elsewhere herein, inactivated bacteria may e.g. be killed or naturally dead bacterial cells, attenuated cells (e.g. attenuated by directed or non-directed mutation), or a component comprising one or more antigenic part(s) thereof.

A "pharmaceutically acceptable excipient" as referred to herein, refers to an optional component of the vaccine for instance one or more emulsifiers, which may facilitate the handling, storage and/or administration thereof, such as presenting the vaccine in a suitable form, e.g. as a gel or liquid, for administration. One example of an excipient used herein is standard PBS (phosphate-buffered saline), but the invention is not limited thereto.

When the term "about" is used herein for a value, this refers to a deviation of a value of ±10%.

"Bizioniosis" is a disease herein characterized by tail- and fin rot, infection on the tip of the mandibular, in particular, but also on the tip if the maxilla which may spread along the mandibula caudally, eye infection, ulcers behind the pectoral fins and alongside the body, and/or septicaemia. In particular, bizioniosis is characterized by these symptoms being caused by bacteria of the genus *Bizionia*, such as *Bizionia piscinecroseptica*, such as *Bizionia piscinecroseptica* 130524K2F7.

"Friggiosis" is a disease defined herein characterized by septicemia (in particular with a high number of bacteria in head kidney and liver), mottled bleedings in a fatty degenerated liver, ascites in the abdomen, ulcers on the skin (such as behind the pectoral fins or spread out on the body) but often no or fewer ulcers on the body than compared to ulcers in winter ulcer and wodanosis, eye infection (which may lead to puncture of the eye), an infection of the tip of the mandibula and/or the tip of the maxilla. Friggiosis may be characterized by being caused by bacteria of the novel species *Aliivibrio friggiae*, such as *Aliivibrio friggiae* 130206K7F2 506.

Flexibacteriosis (marine) is caused by *Tenacibaculum maritimum* (formerly, *Cytophaga marina, Flexibacter marinus* and *F. maritimus*) Several other names as gliding bacterial diseases of sea fish, eroded mouth syndrome and black patch necrosis has been used to designate the disease caused by this bacterium. Marine flexibacteriosis is widely distributed in cultured and wild fish in Europe, Japan, North America and Australia. The disease has been reported among the cultured fish as turbot, sole, gilthead seabream, seabass, red seabream, black seabream (*Acanthopagrus schlegeli*), flounder and salmonids. Although both adults and juveniles may be affected by marine flexibacteriosis, younger fish suffer a more severe form of the disease. Increased prevalence and severity of the disease is observed at higher temperatures (above 15° C.). The disease is influenced by many environmental (stress) and host-related factors (skin condition). In general, the affected fish have eroded and haemorrhagic mouth, ulcerative skin lesions, frayed fins and tail rot. A systemic disease can occur involving different internal organs. The loss of the epithelial fish surface, a typical change of the disease, is probably portal of entry for other bacterial or parasitic pathogens (Toranzo et al 2005).

Bacterial cold water disease (BCWD) (Cipriano and Holt 2005, Izumi and Aranashi 2004) Fish infected with typical BCWD have lesions on the skin and fins. Fins may appear, split, torn, ragged, frayed and may even be eroded totally. Affected fish are often lethargic and stop feeding. Infection may spread septicemically. Salmonid fish can develop a chronic form of BCWD-following recovery from typical BCWD. It is characterised by "corkscrew" swimming, blackened tails and spinal deformities. *Flavobacterium psychrophilum* is considered to be the causative agent of both BCWD and Rainbow trout fry syndrome.

Rainbow trout fry syndrome is an acute disease with high mortality rates. Infected fish may show signs of lethargy, inappetance and exopthalmos before death (Nematollahi et al 2003). The clinical signs of *F. psychrophilum* infections as well as the mortality rate depend on the size of the affected. In coho salmon, which are highly susceptible, the mortalities can be as high as 50%. In fingerlings, a dark pigmentation on one side of the body and erosion of the peduncle area with concomitant exposure of the spinal cord and tail loss are common findings.

Wodanosis is characterized by septicemic infection resulting in ascites, mottled liver, swollen spleen, skin ulcers, and/or fin rot typically on the bases of the tail fin and back fin. Wodanosis may be caused by *Aliivibrio wodanis*. Wodanosis is further described in WO 2013/171236.

DETAILED DESCRIPTION

The inventor of the present document has surprisingly found that the clinical picture of winter ulcer is far more complex than one has previously thought and that other bacteria in addition to *M. viscosa* are involved in causing the symptoms of disease.

The present inventor has found that bacteria of the genus *Bizionia* are involved in causing disease in fish, the clinical picture of which resembles the one of winter ulcer, flexibacteriosis, bacterial cold water disease (BCWD) and/or rainbow trout fry syndrome Bacteria of the genus *Bizionia* have previously been isolated from marine environments and characterized (see e.g. Bowman et al. (2005) which also provides a phylogenetic tree of the family flavobacteriaceae indicating the position of bacteria of the *Bizionia* genera). However, *Bizionia* sp. has previously not been identified as being involved in causing disease in any organism. In particular, the present inventor has identified a novel species of *Bizionia*, hereby denoted *Bizionia piscinecroseptica*, (e.g. exemplified by *Bizionia piscinecroseptica* 130524K2F7) which is shown herein to be involved in a very aggressive disease in fish.

An exemplary strain of *Bizionia piscinecroseptica*, *Bizionia* sp. 130524K2F7 (herein also called *Bizionia piscinecroseptica* 130524K2F7), isolated in Norway, has been deposited according to the Budapest Treaty on Oct. 24, 2013, at the National Collection of Industrial, Food and Marine Bacteria (Ferguson Building, Craibstone Estate, Bucksburn, Aberdeen, AB21 9YA, Scotland, United Kingdom) and been assigned accession number NCIMB 42183. The depositor is the Norwegian School of Veterinary Science ("Norges veterinærhøgskole"), Post Box 8146 Dep, 0033 Oslo, Norway). The *Bizionia* sp. 130524K2F7 is a biologically pure strain.

The present document is therefore directed to compositions comprising bacteria of the genus *Bizionia*, in particular *Bizionia piscinecroseptica*, such as *Bizionia* sp. 130524K2F7 and the use of such compositions as vaccines in the treatment and/or prevention of disease in fish.

Isolation and Characterization of *Bizionia piscinecroseptica* 130524K2F7

The bacterium *Bizionia* sp. 130524K2F7 was isolated from the gills of an Atlantic salmon in Norway in a population of 150 individuals with a natural outbreak of fin rot and septicaemia in a research tank of 1400 liters natural seawater with a temperature of 6.5° C. with supplement of 1000 liters per hour from a depth of 70 meter in the Oslofjord at the Marine Research Station, Norwegian Institute of Water Research, Solbergstrand 8 km south of Drøbak city. The bacterium was isolated on marine agar (Difco) hydrated with aged natural marine water. A few colonies grew as a minor part of a mixed culture with various marine bacteria after 6 days in 8° C. The colonies had a bright golden yellow colour and a size of 1 to 2 mm with a convex, round shape, a butyrous consistency and a regular edge. The bacterial cells were Gram-negative rods with the size of 0.3-0.5×1-3 μm. Secondary growth occurred at blood agar (5% cattle blood in Blood agar base 2, Difco) with good growth after 3 days at a temperature range from +4 to +30° C. No growth at 37 and 43° C. was registered. Growth occurred at 0.5% and 2.5% NaCl, but was clearly better at 0.9% NaCl. The growth was clearly better at +0.9% than at 2.5% NaCl, and growth occurred at 0.5 NaCl.

DNA sequencing of the 16S rDNA gene gave in BLAST alignment best similarity to three isolates of *Bizionia* sp. obtained from the water of the glacial subarctic marine fjord Kongsfjorden in the Svalbard archipelago. These isolates (KJF10-2, KJF12-2 and KJF12-3) are described in Prasad et al. 2013 (Curr. Microbiol., DOI 10.1007/s00284-013-0467-6, In Press). However, there is a 3 bp difference in the 16S rDNA sequence indicating that *Bizionia* sp. 130524K2F7 belongs to another subspecies or species.

As mentioned above, *Bizionia* sp. 130524K2F7 has been deposited at the National Collection of Industrial, Food and Marine Bacteria, Aberdeen, Scotland, United Kingdom and assigned the accession number NCIMB 42183. The isolate is biologically pure.

Growth and Maintenance of *Bizionia* sp.

*Bizionia* sp. 130524K2F7 grows well on blood agar with 5% cattle blood and on Marine agar (DIFCO) made with natural sea water. It grows strongly on Luria Broth, and while growth occurs at various NaCl concentrations, best growth is obtained at about 0.9% NaC. It grows at temperatures from about +4° C. or lower to +30° C. with almost equal growth rate. The strain can be stored at −80° C. in Luria Broth added with 10% glycerol.

The above growth conditions may also suitably be used for growing and maintaining other bacteria of the genus *Bizionia*, such as the species *Bizionia piscinecroseptica*.

Pathogenic Activity of *Bizionia* sp.

*Bizionia piscinecroseptica* (herein as demonstrated by *Bizionia piscinecroseptica* 130524K2F7) was found to infect farmed Atlantic salmon in sea water in particular during the four first weeks after sea-launch as smoltified individuals (see experimental section). The disease was found to occur typically as fin rot (necrosis) in particular at the tail fin and both breast fins (FIGS. 10-14, 16, 18, 22, and 23-28). However, all fins may be infected. The soft tissue of the fins is necrotized and the bony rays may puncture the skin surface in particular behind the breast (pectoral) fins caused by the particular active motility of these fins. The punctured skin quickly was found to develop into an ulcer that ultimately may perforate the abdominal wall exposing the internal organs of the abdomen directly to sea water. In the rearing tanks with infection caused by *Bizionia* sp. the salmon individuals with necrotized fins may puncture the skin of other individuals in the population causing ulcers at various parts of the fish body (FIGS. 22, 29, 30 and 36). This scenario was seen in tanks where the fish panics and seeks to the bottom together or change direction of the swimming pattern.

The necrosis of the fins was found to develop fast and within a few hours major areas of the fins may become grey-white in colour and within a day or so the soft tissue and often the bony spines may be lost.

Infection with *Bizionia piscinecroseptica* on the tip of the mandibula in particular, but also on the tip if the maxilla was found to sometimes also spread along the mandibula caudally leaving the mandibular bones hanging freely in the water without soft tissue. This renders the salmon without ability to eat and the affected individuals may loose weight and often look unusually slender and long. Infection on the maxilla tip may in some cases develop such that the soft tissue is completely lost from the face.

Single fish individuals that have been in the sea for some months were also commonly found to have one infected eye. The infection may primarily puncture the eye but most often undermines and necrotizes the soft tissue behind the eye bowl. During this phase of the eye infection one or both eyes may protrude clearly in a marked exophtalmus before the eye is lost completely or punctured leaving only the empty eye bulb left in the skull.

The various ulcers found herein to be caused by infection with *Bizionia piscinecroseptica* were found to be normally co-infected with other bacteria like *Aliivibrio wodanis, Tenacibaculum* sp, *Aliivibrio friggiae, Moritella viscosa* and various *Vibrio* species, various *Photobacter* species, *Aliivibrio logei* and more. These bacteria produce a biofilm-like layer covering the ulcer. In particular *A. wodanis* at all relevant temperatures and *M. viscosa* at temperatures below 8° C. contributes strongly to ulcer development.

*Bizionia piscinecroseptica* was found to produce septicaemia in infected fish and the fish dies as a result of the septicaemia. Often other bacteria, like in particular *A. wodanis* at all relevant temperatures and *M. viscosa* at temperatures below 8° C. contribute strongly to the septicaemia and death. Often *Aliivibrio friggiae* contributes to the septicaemia (FIGS. 35 through 38). *Aliivibrio logei* is also often isolated from blood and various organs and often in close cell-to-cell contact with *A. wodanis*. During pathogenesis the role of *A. logei* seems to be preventive as opposed to that of *A. wodanis*.

During the pathogenesis of *Bizionia* sp. septicemic infection, *A. wodanis*, *Aliivibrio friggiae* and *A. logei* multiply in the intestine of the salmon and are transported across the gut wall into the blood circulatory system. In particular, *A. wodanis* was found to contribute significantly to the pathogenesis in approximately 80 to 90% of Atlantic salmon dying from the complex infection.

It has so far not been possible to cultivate *Bizionia* sp. from the tissues of infected fish despite it being present at high concentrations in the tissue and it has not previously been identified in tissues of infected fish. The present inventor surprisingly found that it was possible to isolate *Bizionia* sp. from the environment surrounding infected fish including the gills.

*Bizionia* sp. may produce heavy loss (up to approx. 80% of the population) during the first 4 weeks after sea-launch of the Atlantic salmon smolts. However, the surviving population regularly develops natural immunization if there has been some loss caused by fin rot and septicaemia in the population after sea-transfer.

Other fish species like goldsinny wrasse (*Ctenolabrus rupestris*) that are used as cleaner fish for salmon lice in Atlantic salmon farms are developing "bizioniosis" with the same symptoms and pathogenetic changes as in Atlantic salmon.

The experience is that the "smolt syndrome" can be prevented by keeping the smolts on brackish water (2%). However, to stop the mortality from the "smolt syndrome" without antibiotics brackish water with only 1% salt is needed.

*Bizionia piscinecroseptica* and and/or other *Bizionia* species may cause disease in both fresh and salt water and may be the primary causative agents behind the majority of the fin rot diseases or flexibacteriosis in both marine and fresh water including bacterial cold water disease (BCWD) and rainbow trout fry syndrome in fresh and brackish water. These diseases are so far been linked to *Tenacibaculum maritimum*, *Flavobacterium psychrophilum*, *Flavobacterium columnare* including other bacteria in these genera. Bacteria in the *Tenacibaculum* and *Flavobacterium* genera are contributing to disease but mainly secondary to an until now unrecognized bizioniosis caused by the *Bizionia piscinecroseptica* and/or its relatives in the *Bizionia* genus.

Consequently, the disease caused by *Bizionia piscinecroseptica* and/or its relatives in the *Bizionia* genus is herein denoted bizioniosis and is characterized by e.g. fin rot, infection on the tip of the mandibula, in particular, but also on the tip if the maxilla which may spread along the mandibula caudally, eye infection, ulcers, and/or septicaemia. A full protection against bizioniosis and thereby most of the flexibacteriosis in marine and fresh water including "rainbow trout syndrome" and "bacterial cold water disease" in rainbow trout could according to the present document be gained by controlling the *Bizionia* bacteria in the production cycle of the various farmed fish species of relevance.

Compositions

The compositions according to the present document comprise bacteria of the genus *Bizionia* (i.e. *Bizionia* sp) and/or an antigen thereof. Examples of *Bizionia* sp. which may be used in a composition according to the present document include, but is not limited to *Bizionia saleffrena*, *Bizionia gelidisalsuginis*, *Bizionia paragorgiae*, *Bizionia myxarmorum*, and *Bizionia algoritergicola*. In particular the *Bizionia* sp. may be *Bizionia piscinecroseptica*, such as *Bizionia piscinecroseptica* 130524K2F7, further disclosed elsewhere herein. The composition disclosed herein may also be denoted a "vaccine composition" or a "vaccine" as it may be used for vaccination purposes in the treatment and/or prevention of disease.

The compositions of the present document may comprise bacterial cells of the *Bizionia* sp. or an antigen thereof. As explained elsewhere herein, in the context of the present document, the term "antigen" includes a bacterial cell(s), a bacterial extracellular product, a protein or part thereof produced by the bacterium, or any other bacterially produced substance/component.

As mentioned above, the antigen may be an extracellular product of bacterial cells. An extracellular product as referred to herein may e.g. be the used growth medium which has been used during culturing of the bacterial cells after removal of the bacterial cells, e.g. by centrifugation to obtain a supernatant. An extracellular product may also refer to one or more single substances/components isolated from the growth medium of the bacterial cells, such as a protein or part thereof.

The composition according to the present document may comprise inactivated bacteria. The term "inactivated bacteria" refers to bacteria which due to one or more modifications have lost their virulence, but which still induces an immune response in a recipient, e.g. a fish, which is sufficient to provide an immunizing effect. Means and methods for inactivating bacteria are disclosed elsewhere herein and include e.g. the use of formalin, heat inactivation, inactivation by use of radiation or antibiotics, and attenuation of bacterial cell.

A composition according to the present document can further comprise an adjuvant and/or a pharmaceutically acceptable excipient.

In addition to the inactivated bacteria, and/or one or more components and/or antigenic part(s) thereof and/or adjuvants in a vaccine composition, emulsifiers (emulgator) may be added, such as highly refined polyoxyethylenesorbitan and sorbitan oleates, such as polysorbate 85, polysorbate 80, PEG-6 sorbitan oleate, and sorbitan oleate etc. Emulsifiers are added to stabilize the vaccine emulsion in particular when mineral oils are added as adjuvant. When oil-in-water or water-in-oil emulsions are made they may be instable if not used soon after. It is also possible to instead if adding an external emulgator, to emulsify mechanically and use the vaccine the same day as it is prepared. For vaccines that need to be stored, emulsifiers are often added in a mixture of up to typically 3 to 4 in accordance with procedures known to the manufacturer. A successful emulsifier-mix makes it possible to store the vaccine effectively for a longer period.

Typically from 5% and up to 10 or 12% emulsifier can be part of a commercial vaccine composition. However, methods and means for preparing a vaccine composition suitable for storage are well known for the skilled practitioner within this field.

Vaccine components may be in liquid form both as hydrophilic and lipophilic, which may often then be mixed in emulsions that need to be stabilized for storage. Examples may be found in Roar Gudding (Editor) et al. "Fish Vaccinology", Developments in Biological Standardization, 484 pages.

In addition, dry vaccines may also be prepared from the compositions as disclosed herein, and then dissolved before usage. This is particularly for, dip, bath or oral vaccines that are not using oil adjuvants or the like.

As bizioniosis (i.e. the disease caused by *Bizionia* sp, in particular *Bizionia piscinecroseptica* as defined elsewhere herein) develops in a concerted action with other infections like wodanosis, winter ulcer, friggiosis, cold water vibriosis and vibriosis it is preferable to include one or more of bacteria causing these disease in the composition. Preferably all the causative agents causing these diseases should be included to fully protect fish, such as Atlantic salmon, also in the first weeks in the sea.

It seems like *Bizionia* sp. almost regularly "opens" the fish directly and indirectly to infections with other bacterial pathogens (and possibly viruses) through more or less extensive tail and fin rot.

A composition according to the present document may thus preferably further comprise bacteria of two or more other genera and/or species and/or an antigen of such bacteria. Examples of such bacteria include, but are not limited to bacteria of the species *Moritella* viscose, *Aliivibrio wodanis, Tenacibaculum* sp, such as *Tenacibaculum maritimum, Vibrio* sp, *Photobacter* sp, *Aeromonas salmonicida* ss *salmonicida, Aliivibrio logei, Aliivibrio salmonicida, Flavobacterium*, such as *Flavobacterium psychrophilum* and *Flavobacterium columnare, Aliivibrio friggiae* (for a characterization and an exemplary strain, see elsewhere herein) and *Vibrio anguillarum*. A composition according to the present document may therefore comprise one or more of such further bacteria and/or antigens thereof.

As disclosed elsewhere herein, a composition may comprise an antigen produced by the growth of a bacterium as a single culture. However, the composition may also comprise antigens which have been produced in mixed cultures comprising two or more different bacterial strains, species and/or genera. Such a mixed culture may comprise any combination of the bacteria disclosed herein, e.g. any combination of *Bizionia* sp, such as *Bizionia piscinecroseptica* (e.g. *Bizionia piscinecroseptica* 130524K2F7), *Moritella viscosa, Aliivibrio wodanis, Tenacibaculum* sp, such as *Tenacibaculum maritimum, Vibrio* sp, *Photobacter* sp, *Aeromonas salmonicida* ss *salmonicida, Aliivibrio logei, Aliivibrio salmonicida, Flavobacterium*, such as *Flavobacterium psychrophilum* and *Flavobacterium columnare, Aliivibrio friggiae* and *Vibrio anguillarum*. In particular it may be preferable to culture *Moritella viscosa, Aliivibrio wodanis* together. *A. wodanis* and *M. viscosa* cultivated as a co-culture in addition to single cultures could be included in the vaccine. The same is the case with *A. wodanis* and *A. friggiae*. Growing the bacteria in mixed cultures may change the antigenic presentation of the bacteria and may thus be important in order to provide a composition the antigenic presentation of which better mimics the situation in nature, where there is a complex interaction between bacteria involved in causing and protecting fish from disease.

An exemplary composition may comprise or consist of antigens, such as inactivated bacterial cells, from strain(s) of the following bacterial species: *M. viscosa* and *Bizionia* sp. (e.g. *Bizionia piscinecroseptica*, such as *Bizionia piscinecroseptica* 130524K2F7).

Another exemplary composition may comprise or consist of antigens, such as inactivated bacterial cells, from strain(s) of the following bacterial species: *A. wodanis* and *Bizionia* sp. (e.g. *Bizionia piscinecroseptica*, such as *Bizionia piscinecroseptica* 130524K2F7).

Another exemplary composition may comprise or consist of antigens, such as inactivated bacterial cells, from strain(s) of the following bacterial species: *M. viscosa, A. wodanis*, and *Bizionia* sp. (e.g. *Bizionia piscinecroseptica*, such as *Bizionia piscinecroseptica* 130524K2F7).

Another exemplary composition may comprise or consist of antigens, such as inactivated bacterial cells, from strain(s) of the following bacterial species: *Bizionia* sp. (e.g. *Bizionia piscinecroseptica*, such as *Bizionia piscinecroseptica* 130524K2F7) and *Aliivibrio friggiae*, such as *Aliivibrio friggiae* 130206K7F2 506.

Another exemplary composition may comprise or consist of antigens, such as inactivated bacterial cells, from strain(s) of the following bacterial species: *M. viscosa, A. wodanis, Bizionia* sp. (e.g. *Bizionia piscinecroseptica*, such as *Bizionia piscinecroseptica* 130524K2F7), and *Aliivibrio friggiae*, such as *Aliivibrio friggiae* 130206K7F2 506.

A composition may also comprise antigen(s) from *M. viscosa*, such as, but not limited to, *M. viscosa* 06/09/139 Ft5427 (deposition number NCIMB 42122). *M. viscosa* 06/09/139 Ft5427 (deposition number NCIMB 42122) has been deposited according to the Budapest Treaty at the National Collection of Industrial, Food and Marine Bacteria (NCIMB Ltd., Ferguson Building, Craibstone Estate, Bucksburn, Aberdeen, AB21 9YA, Scotland) by the depositor Norwegian School of Veterinary Science ("Norges veterinærhøgskole"), Post Box 8146 Dep, 0033 Oslo Norway on Mar. 7, 2013. This strain is publically available from the Norwegian School of Veterinary Science and further described in the publications Karlsen et al. 2012, and Bjørnsdottir et al. 2012.

Any of the vaccines (vaccine compositions) disclosed herein may further comprise any other antigen, such as antigens commonly employed in commercially available vaccines.

Methods for preparing a composition according to the present document are disclosed elsewhere herein. The present document is also directed to a composition obtained or obtainable by any such method.

Method for Producing the Compositions

A vaccine (herein also denoted a vaccine composition and the like) may be produced by any commonly recognized method for vaccine production. As mentioned elsewhere herein, such a composition comprises *Bizionia* sp. and/or an antigen thereof, in particular *Bizionia piscinecroseptica*, (e.g. *Bizionia piscinecroseptica* 130524K2F7). A method for producing a vaccine may e.g. comprise the steps of growing bacterial cells, as single or mixed cultures and inactivating the bacterial cells e.g. by formalin, heat, radiation, attenuation and/or antibiotics. Such a method may further comprise the steps of separating the bacterial cells from their growth medium (e.g. by centrifugation or filtration) and further optionally washing the bacterial cells (e.g. by resuspension in a suitable liquid, such as a common salt buffer). As mentioned elsewhere herein, extracellular products of the bacterial cells may also be used as antigens. An extracellular product as referred to herein may e.g. be the used growth medium of the bacterial cells. The extracellular product may consequently e.g. comprise a supernatant of used growth medium prepared by separating the bacterial cells from the used growth medium e.g. by centrifugation or filtration. The used growth medium may comprise products excreted from the bacterial cells as well as parts of bacterial cells resulting from e.g. lysis of the cell. An extracellular product may also refer to one or more single substances/components isolated from the growth medium of the bacterial cells, such as a protein.

A method for preparing a composition according to the present document may therefore comprise the steps of:
a) cultivating the desired bacteria alone or in combination with other bacteria;
b) optionally separating said bacteria from their growth medium;
c) inactivating said bacteria;
d) optionally mixing said bacteria with a pharmaceutically acceptable excipient and/or adjuvant.

Bacteria suitable for being provided in a composition are disclosed elsewhere herein.

The bacteria used for preparing a vaccine may be grown as single or as mixed cultures. By single culture is in the context of the present document intended a culture containing only one type of a bacterial strain, i.e. a pure culture. A mixed culture refers to a culture containing a mixture of at least two different types of bacteria which e.g. may be different strains of the same bacterial species and/or different bacterial species. In such a mixed culture, the cells may be cultured in a way that creates physical cell-cell contact between the cells of at least two species. By growing different strains and/or species of bacteria together, the antigenic presentation of the bacteria may be different as compared to when grown as single cultures. Also, different mixed cultures containing different mixtures of bacterial cells may result in different antigenic presentation by the cells. It may thus be valuable for a vaccine to include an array of different bacterial cells grown in both single and mixed cultures. It is also possible to obtain the effect of a mixed culture by growing one or more types of bacteria in the presence of a factor, such as an extracellular product, isolated from another bacterium or the used growth medium of one or more other bacteria grown as single or mixed cultures. Exemplary other bacteria to grow the *Bizionia* sp. together with include, but is not limited to, another *Bizionia* sp, *Bizionia piscinecroseptica*, *Moritella viscose*, *Aliivibrio wodanis*, *Tenacibaculum* sp, *Tenacibaculum maritimum*, *Vibrio* sp, *Photobacter* sp, *Aeromonas salmonicida* ss *salmonicida*, *Aliivibrio logei*, *Aliivibrio salmonicida*, *Flavobacterium*, *Flavobacterium psychrophilum*, *Flavobacterium columnare*, *Aliivibrio friggiae* and/or *Vibrio anguillarum*.

When *Aliivibrio friggiae*, such as *Aliivibrio friggiae* 130206K7F2 506, is grown in the presence of *A. wodanis*, a percentage of salt, such as NaCl, of about 0.5-1.2%, such as about 0.7-1.1%, about 0.8-1.0%, e.g. about 0.9% may be used, due to the clear inhibitory activity by *A. wodanis* against *A. friggiae* observed at this salinity.

When preparing a composition according to the present document, two or more single and/or mixed cultures may be prepared and thereafter mixed with each other in order to provide a composition comprising an array of different bacterial species grown under different conditions in order to be able to prepare a composition that provides a broad immunity against different bacteria.

Normally formalin is used for inactivating bacteria included in vaccine preparations. Formalin inactivation of bacteria may typically be performed by adding formalin to a bacterial culture, such as about 1% formalin, for e.g. two hours, before washing the killed bacteria. However, formalin is considered to be an active denaturing agent of proteins resulting in discrepancy between the acquired immunological memory based on denatured bacterial surface proteins and the natural proteins of the pathogen approaching the host. This "blurred" image of the pathogen may be sharper by inactivating the bacterial cells prepared for the vaccine by a temperature above the level these psychrophilic bacteria can survive but still below the temperature when the bacterial proteins denature by heat, typically above 40-42° C. This principle of inactivation is an example of an elegant way of inactivating psychrophilic bacterial pathogens for vaccine preparation. The same sharp immunological memory image of the outlook of the pathogen is also acquired by inactivating the bacteria by radiation or chemicals degrading specifically the nucleic acids. When this is noted there are studies indicating that in general formalin-killed bacteria may be stronger antigens and thereby causing a better immune reaction than the natural antigens. Therefore formalin may be an alternative component of the vaccine preparations disclosed herein for this reason.

Heat may also be used as an inactivation method, such as by heating the bacteria to about 30° C. for a time period sufficient for inactivating the bacteria, such as e.g. about 16 hours. The heat inactivation with relatively low temperature keeps the antigens natural without being denatured, and is therefore particularly useful in the present context. An example of a heat inactivation procedure for inactivating bacteria comprises growing bacterial cultures to late logarithmic phase and inactivating the bacteria by heating the cultures to about 30° C. for about 16 hours without emptying the cultures from the culture flasks and without adding any extra component(s).

Attenuation as a means for effecting inactivation of bacteria may be performed by repeated cultivations with or without mutagenic chemicals in the culture, by radiation or any other relevant measure until random mutations occur in one or more genes relevant for a successful pathogenesis. Alternatively attenuation of the bacteria by directed knock-out mutations of one or more of the virulence genes may be used. Attenuation of the bacteria thus means a weakening of the bacteria so that their ability to cause disease is reduced or lost while they are still able to induce an immune response when administered to a subject.

The viability of the bacterial cells after inactivation may be controlled by cultivation on a suitable growth medium.

Medical Use of the Compositions

As mentioned elsewhere herein, the present document for the first time discloses that bacteria of the genus *Bizionia* are involved in causing disease. Also, the document for the first time discloses bacteria of the species denoted *Bizionia piscinecroseptica*.

Consequently, the present document is directed to a composition as disclosed herein comprising *Bizionia* sp, and/or an antigen thereof for medical use. The composition for all medical uses is disclosed elsewhere herein. Likewise, *Bizionia* species and strains are disclosed elsewhere herein, and include e.g. *Bizionia piscinecroseptica* and *Bizionia piscinecroseptica* 130524K2F7.

The present document is also directed to a composition as disclosed herein comprising *Bizionia* sp, such as *Bizionia piscinecroseptica* or *Bizionia piscinecroseptica* 130524K2F7, and/or an antigen thereof for use as a vaccine. Due to the strong pathogenic activity that is demonstrated herein for *Bizionia* bacteria, immunization against this bacterium is important for protection of fish (see Experimental section).

The present document also for the first time discloses a disease herewith denoted bizioniosis. Bizioniosis is, as disclosed elsewhere herein, characterized by fin rot, infection on the tip of the mandibular, in particular, but also on the tip if the maxilla which may spread along the mandibula caudally, eye infection, ulcers, and/or septicaemia. In particular, bizioniosis is characterized by these symptoms caused by *Bizionia* sp, such as *Bizionia piscinecroseptica*, such as *Bizionia piscinecroseptica* 130524K2F7.

The present document also for the first time discloses a disease herewith denoted friggiosis. Friggiosis is characterized by septicemia (in particular with a high number of bacteria in head kidney and liver), mottled bleedings in a fatty degenerated liver, ascites in the abdomen, ulcers on the skin (such as behind the pectoral fins or spread out on the body), eye infection (which may lead to puncture of the eye), an infection of the tip of the mandibula and/or the tip of the maxilla (FIGS. 1 to 30 and 36 to 43). Friggiosis may be characterized by being caused by bacteria of the novel species *Aliivibrio friggiae*, such as *Aliivibrio friggiae* 130206K7F2 506.

Consequently, the present document is also directed to a composition as disclosed herein comprising *Bizionia* sp, such as *Bizionia piscinecroseptica*, such as *Bizionia piscinecroseptica* 130524K2F7, and/or an antigen thereof for use for the treatment and/or prevention of bizioniosis.

The present document is also directed to a composition as disclosed herein comprising, *Bizionia* sp, such as *Bizionia piscinecroseptica*, such as *Bizionia piscinecroseptica* 130524K2F7, and/or an antigen thereof, and *Aliivibrio friggiae*, such as *Aliivibrio friggiae* 130206K7F2 506, and/or an antigen thereof for use for the simultaneous treatment and/or prevention of bizioniosis and friggiosis.

The present document is also directed to a composition as disclosed herein comprising *Bizionia* sp, such as *Bizionia piscinecroseptica*, such as *Bizionia piscinecroseptica* 130524K2F7, and/or an antigen thereof, and *Aliivibrio wodanis*, and/or an antigen thereof, for use for the simultaneous treatment and/or prevention of bizioniosis and wodanosis.

Any composition according to the present document may also comprise *M. viscosa* for use for the simultaneous treatment and/or prevention of winter ulcer.

The present document is also directed to a composition as disclosed herein comprising *Bizionia* sp, such as *Bizionia piscinecroseptica*, such as *Bizionia piscinecroseptica* 130524K2F7, and/or an antigen thereof, *Aliivibrio friggiae*, such as *Aliivibrio friggiae* 130206K7F2 506, and/or an antigen thereof, and *Aliivibrio wodanis*, and/or an antigen thereof, for use for the simultaneous treatment and/or prevention of bizioniosis, friggiosis, and wodanosis.

The present disclosure is also directed the use of *Bizionia* sp, such as *Bizionia piscinecroseptica*, such as *Bizionia piscinecroseptica* 130524K2F7, and/or an antigen thereof or a composition as defined herein for the manufacture of a medicament, such as a vaccine, for the treatment and/or prevention of bizioniosis.

The present disclosure is also directed the use of *Bizionia piscinecroseptica*, such as *Bizionia piscinecroseptica* 130524K2F7, and/or an antigen thereof, and *Aliivibrio friggiae*, such as *Aliivibrio friggiae* 130206K7F2 506, and/or an antigen thereof, for the manufacture of a medicament, such as a vaccine, for the simultaneous treatment and/or prevention of bizioniosis and friggiosis.

The present disclosure is also directed the use of *Bizionia piscinecroseptica*, such as *Bizionia piscinecroseptica* 130524K2F7, and/or an antigen thereof, and *Aliivibrio wodanis*, and/or an antigen thereof, for the manufacture of a medicament, such as a vaccine, for the simultaneous treatment and/or prevention of bizioniosis and wodanosis.

The present disclosure is also directed the use of *Bizionia piscinecroseptica*, such as *Bizionia piscinecroseptica* 130524K2F7, and/or an antigen thereof, *Aliivibrio friggiae*, such as *Aliivibrio friggiae* 130206K7F2 506, and/or an antigen thereof, and *Aliivibrio wodanis*, and/or an antigen thereof, for the manufacture of a medicament, such as a vaccine, for the simultaneous treatment and/or prevention of bizioniosis, friggiosis, and wodanosis.

The present document is also directed to the use of *M. viscosa* together with any other bacterium disclosed herein for the preparation of a medicament for the simultaneous treatment and/or prevention of winter ulcer.

The present disclosure is also directed to a method for treating and/or preventing bizioniosis comprising the administration of a pharmaceutically effective amount of composition as disclosed herein comprising *Bizionia* sp, such as *Bizionia piscinecroseptica*, such as *Bizionia piscinecroseptica* 130524K2F7, and/or an antigen thereof to a subject in need thereof.

The present disclosure is also directed to a method for simultaneously treating and/or preventing bizioniosis and friggiosis comprising the administration of a pharmaceutically effective amount of a composition as disclosed herein comprising *Bizionia* sp, such as *Bizionia piscinecroseptica*, such as *Bizionia piscinecroseptica* 130524K2F7 and *Aliivibrio friggiae*, such as *Aliivibrio friggiae* 130206K7F2 506, and/or an antigen thereof, to a subject in need thereof.

The present disclosure is also directed to a method for simultaneously treating and/or preventing bizioniosis and wodanosis comprising the administration of a pharmaceutically effective amount of composition as disclosed herein comprising *Bizionia* sp, such as *Bizionia piscinecroseptica*, such as *Bizionia piscinecroseptica* 130524K2F7 and *Aliivibrio wodanis*, and/or an antigen thereof, to a subject in need thereof.

The present disclosure is also directed to a method for simultaneously treating and/or preventing bizioniosis, friggiosis, and wodanosis comprising the administration of a pharmaceutically effective amount of composition as disclosed herein comprising *Bizionia* sp, such as *Bizionia piscinecroseptica*, such as *Bizionia piscinecroseptica* 130524K2F7, *Aliivibrio friggiae*, such as *Aliivibrio friggiae* 130206K7F2 506, and/or an antigen thereof, and *Aliivibrio wodanis*, and/or an antigen thereof, to a subject in need thereof.

A composition as disclosed herein comprising *Bizionia* sp. and/or an antigen thereof may be administered to a subject by any suitable means. For the vaccination of fish suitable administration routs include intraperitoneal injection, bath vaccination and/or oral vaccination.

By the term "subjects" is in the context of the present document intended any subject which may benefit from a treatment and/or prevention as disclosed herein. Subjects suitable for being vaccinated and protected by a vaccine *Bizionia* genus and/or an antigen thereof in accordance with the present document thus includes all fish species with tail- and fin rot related diseases, often called marine flexibacteriosis, that as per today is considered caused by the bacterium *Tenacibaculum maritimum* in both the northern and southern hemisphere such as cultured Atlantic salmon, rainbow trout (*Oncorhynchus mykiss*), turbot (*Scophthalmus maximus* L. and *Psetta maxima maeotica* L. subspecies in the Black sea), halibut (*Plecoglossus altivelis*), sole (*Solea senegalensis* L.), Dover sole (*Solea solea* L.), red sea bream (*Pagrus major* Temminck & Schlegel), black sea bream (*Acanthopagrus schlegeli* Bleeker), rock bream (*Oplegnathus fasciatus* Temminck & Schlegel), flounder (*Paralichthys olivaceus*), striped trumpeter (*Latris lineata*), yellow-eye mullet (*Aldrichetta forsteri* Valenciennes), black bream (*Acanthopagrus butcheri* Munro). Included among fish that would be protected by a vaccine containing antigens from *Bizionia* bacteria would be rainbow trout and various fresh brackish water farmed fish like Nile tilapia (*Oreochromis niloticus*) and Nile catfish (*Clarias gariepinus*) infected with *Flavobacterium psychrophilum, Flavobacterium columnare* and related species in genus *Flavobacterium* (previously *Cytophaga*) causing Bacterial Cold Water Disease (BCWD) and rainbow trout fry syndrome in various European countries including France, Germany, Denmark and Sweden and also recently Norway (flavobacteriosis in rainbow trout raised in the inner Sognefjord), in Egypt and various African, Asian and South, Middle and North-American countries farming tilapia, catfish and cyprinid fish like and other fresh water fish species. *F. psychrophilum* was originally isolated from the Pacific coho salmon (*Oncorhynchus kisutch*) in USA in 1948 and has during the last years been reported as a cause of BCWD and rainbow trout syndrome in USA, Europe, Japan, Australia, Chile and Korea in several freshwater species like e.g., eel (*Anguilla anguilla*), common carp (*Cyprinus carpio*), crucian carp (*Carassius carassius*), tench (*Tinca tinca*), and oikawa (*Zacco platypus*). In Japan, since the first isolation of *F. psychrophilum* on a local ayu (*Plecoglossus altivelis*) farm in 1987, the bacterium has spread widely in many host species, such as coho salmon, rainbow trout and oikawa, in various local areas. Because of serious losses in rivers, as well as in fish farms, BCWD caused by *F. psychrophilum* is the most economically important fish disease in Japan (Handlinger et al. 1997, Cipriano & Holt 2005). For example, subjects include fish of the family Salmonidae" (salmonids). Salmonidae includes salmon, trout, chars, freshwater whitefishes and graylings. An example of a fish suitable for being vaccinated with a composition as defined herein is a fish originating from the family Salmonidae, but as mentioned above said composition may also be suitable for vaccinating other fish than salmonids, such as Atlantic cod, turbot and cleaner fish, including five species of wrasse (Labridae), used on fish farms in Norway and to a lesser extent in Scotland, Shetland and Ireland to reduce the infestation of sea lice on the skin of Atlantic salmon.

Kit of Parts

Furthermore is disclosed herein a kit for vaccinating fish, said kit comprising one or more composition(s) of inactivated bacteria (vaccine composition(s)), means for handling said composition(s) and optionally instructions for use. Said means for handling said composition(s) may e.g. be a plastic or other relevant container meant for refilling automated syringes handled manually by vaccinators or for use in robotic devices used for injection of the anaesthetized fish, container with composition meant for preparing working solutions for bath or dip vaccination or tube, prefilled syringes for performing intraperitoneal injection etc., fish feed or similar prepared with the composition intended for oral application but is not limited thereto. Said instructions for use may refer to a method for treating and/or preventing a disease as disclosed herein, including e.g. the amount of vaccine preparation that is to be used. The composition(s) may be contained in any type of container suitable for storage and transport of the composition, such as a plastic, metallic or glass tube or vial.

Aliivibrio wodanis

Aliivibrio wodanis has now also been shown to possess a virulent role in the acute stages of a new disease herein denoted wodanosis, as well as in the chronic stages (co-infection resulting in chronic "winter ulcer") of winter ulcer and wodanosis due to its interaction with the bacterium Moritella viscosa.

Wodanosis as defined elsewhere herein is characterized by e.g. causing skin ulcers and/or septicemia and may be dominated by septicemia in the summer months.

A. wodanis was found to at an early stage infect the small ulcers created by M. viscosa and establish a co-infection together with M. viscosa. By physical contact between the two species of bacterial cells A. wodanis modulates and reduces the virulence of M. viscosa, including down-regulation and inhibition of production of hemolysins and other toxins produced by M. viscosa. Even the cell-growth of M. viscosa is inhibited by A. wodanis at an early stage in the co-infection. A. wodanis also down-regulates its own virulence in co-infection with M. viscose in chronic "winter ulcer".

Due to the importance of A. wodanis in disease in fish farms, it may be preferable to include at least one strain of A. wodanis in a vaccine. As mentioned elsewhere herein, A. wodanis may also be cultured under single culture and/or mixed culture conditions.

A. wodanis ((NVI 88/441$^T$ (=NCIMB 13582$^T$)) is public and available at the National Collection of Industrial, Food and Marine Bacteria, Aberdeen, Scotland and was deposited May 3, 1999 by Henning Sørum, Norwegian School of Veterinary Science/Norwegian College of Veterinary Medicine, Post Box 8146 Dep, 0033 Oslo Norway. It may be commercially obtained therefrom. This type strain is also available from ATCC (American Type Culture Collection, 10801 University Boulevard, P.O. Box 1549, Manassas, Va. 20110 USA (BAA-104 (Aliivibrio wodanis, NVI 88/441$^T$) and from CRBIP (Centre de Ressources Biologiques de l'Institut Pasteur, Institut Pasteur Service des Archives, 28 rue du Dr Roux, 75724 Paris cedex 15, France) (CIP108769 T Aliivibrio wodanis, NVI 88/441$^T$) deposited 2005 by Henning Sørum.

In addition the reference strain of A. wodanis (NVI 06/09/139-Ft 5426 (=NCIMB accession number 42121) has been deposited according to the Budapest Treaty at the National Collection of Industrial, Food and Marine Bacteria (NCIMB Ltd., Ferguson Building, Craibstone Estate, Bucksburn, Aberdeen, AB21 9YA, Scotland) by the depositor Norwegian School of Veterinary Science ("Norges veterinærhøgskole"), Post Box 8146 Dep, 0033 Oslo Norway on Mar. 7, 2013. This strain is also publically available from the Norwegian School of Veterinary Science and further described in the publication Karlsen et al. 2012.

Any A. wodanis strain may be used in a vaccine or for vaccine production according to the present document.

Aliivibrio friggiae

The present inventor has also found that bacteria of a novel species herein denoted Aliivibrio friggiae are involved in causing disease in fish, the clinical picture of which resembles the one of winter ulcer, flexibacteriosis, bacterial cold water disease (BCWD) and/or rainbow trout fry syndrome. An exemplary strain of Aliivibrio friggiae, Aliivibrio sp. 130206K7F2 506 (herein also called Aliivibrio friggiae 130206K7F2 506), isolated in Norway, has been deposited according to the Budapest Treaty on Oct. 24, 2013, at the National Collection of Industrial, Food and Marine Bacteria (Ferguson Building, Craibstone Estate, Bucksburn, Aberdeen, AB21 9YA, Scotland, United Kingdom) and been assigned accession number NCIMB 42181. The depositor is the Norwegian School of Veterinary Science ("Norges veterinærhøgskole"), Post Box 8146 Dep, 0033 Oslo, Norway). The Aliivibrio sp. 130206K7F2 506 is isolated and a biologically pure strain. Aliivibrio sp. 130206K7F2 506 may in the context of the present document also be called Aliivibrio friggiae 130206K7F2 506. The present document is therefore also directed to compositions also comprising bacteria of the novel species Aliivibrio friggiae, such as Aliivibrio sp. 130206K7F2 506, and the use of such compositions as vaccines in the treatment and/or prevention of disease in fish.

Isolation and Characterization of Aliivibrio friggiae

Aliivibrio friggiae (strain 130206K7F2 506) was isolated from a large number of Atlantic salmon that died from ulcers and septicaemia in experiments with salmon that was sea-launched after smoltification and exposed to natural seawater.

The bacterium Aliivibrio friggiae species novo was isolated a few hundred times from kidney, liver, ulcers and intestine of Atlantic salmon individuals with a previously undescribed bacterial infection herein denoted "friggiosis" during three different sets of vaccination experiments performed at the Marine Research Station, Norwegian Institute of Water Research, Solbergstrand 6 km south of Drøbak city from 1 Jul. 2012 to October 2013. The first experiment included a population of 1400 smolts separated in 6 groups of 50 smolts (tank 1) or in 5 groups of 50 smolts (tank 2, 3, 4 and 5) in separate populations in a research tank of 1400 liters natural seawater with a temperature varying from 5.8 to 11° C. during the year. There was an unvaccinated control group in each of the tanks. The sea-water was supplied with 1700 liters per hour from a depth of 70 meter in the Oslofjord at the Marine Research Station, Norwegian Institute of Water Research, Solbergstrand. None of the research vaccines used contained antigens from A. friggiae.

Figure 31:
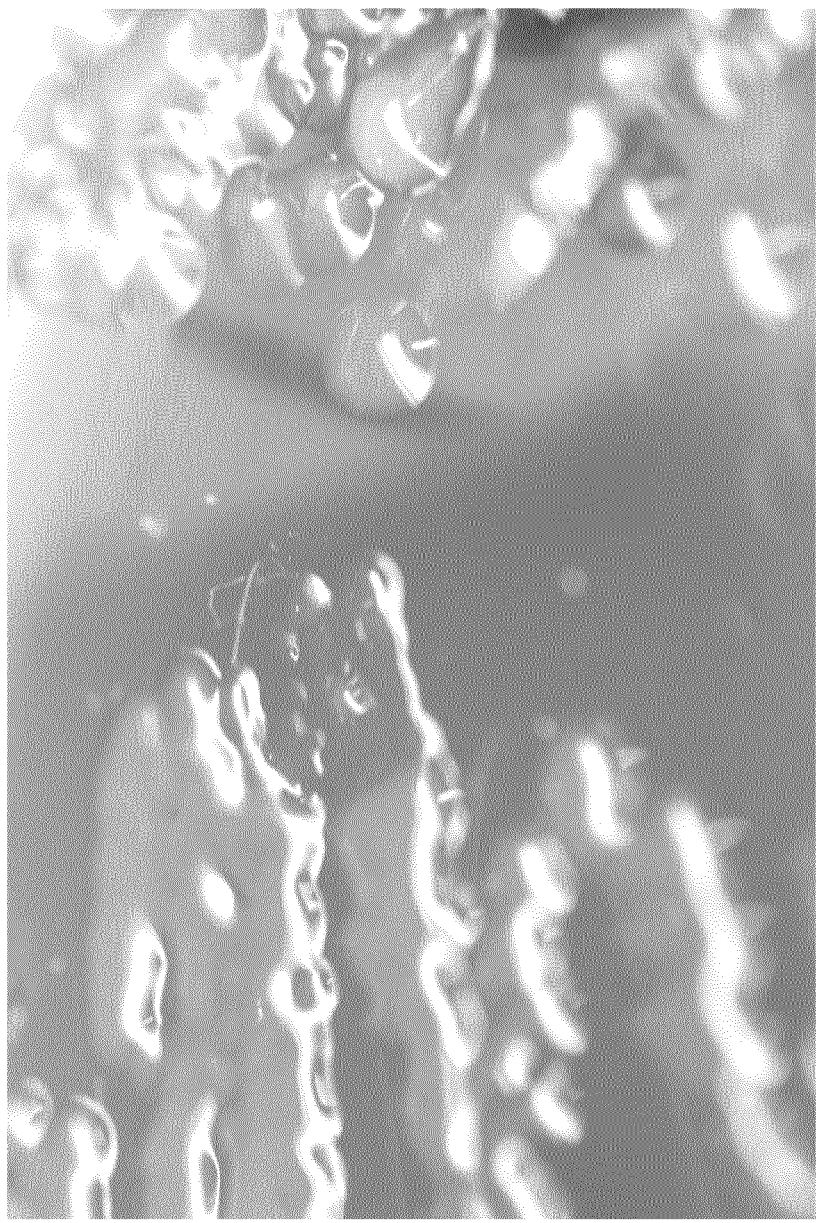
FIG. 31: Rich growth of *Aliivibrio friggiae* distant from one single colony of *Aliivibrio wodanis* a bit left to the middle of the photo. The *A. wodanis* colony has inhibited the growth of the nearby *A. friggiae* on blood agar with 0.9% NaCl.
Figure 32:
FIG. 32: Growth of *Aliivibrio friggiae* colonies (dark grey) in close contact with *Aliivibrio logei* colonies (light grey) from head kidney on blood agar with 2.5% NaCl at 10° C. for 4 days.
Figure 33:
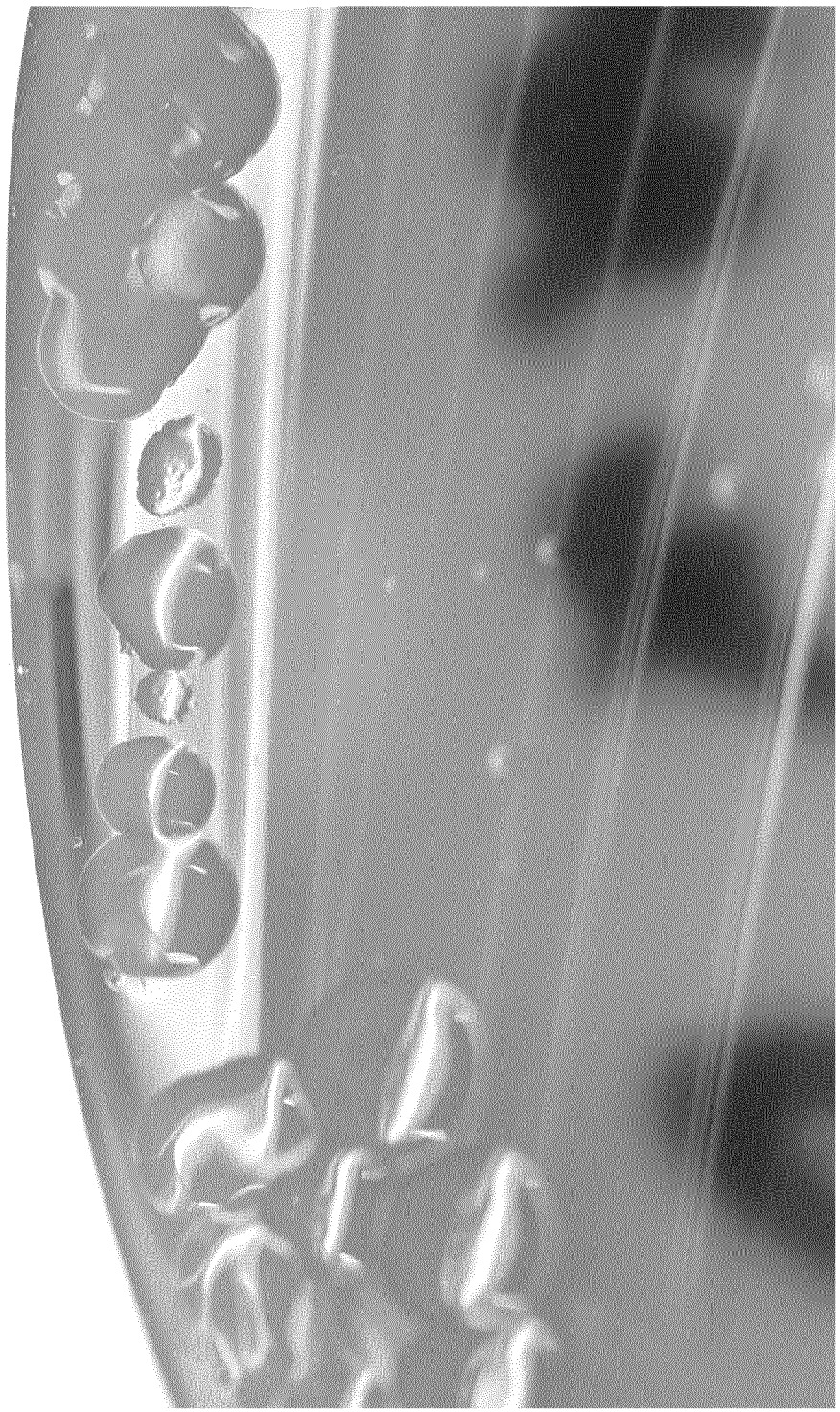
FIG. 33: *Aliivibrio wodanis* colonies (large mucoid) inhibiting *Aliivibrio friggiae* colonies (two flat colonies on each side of a mucoid large *A. wodanis* colony).
Figure 34:
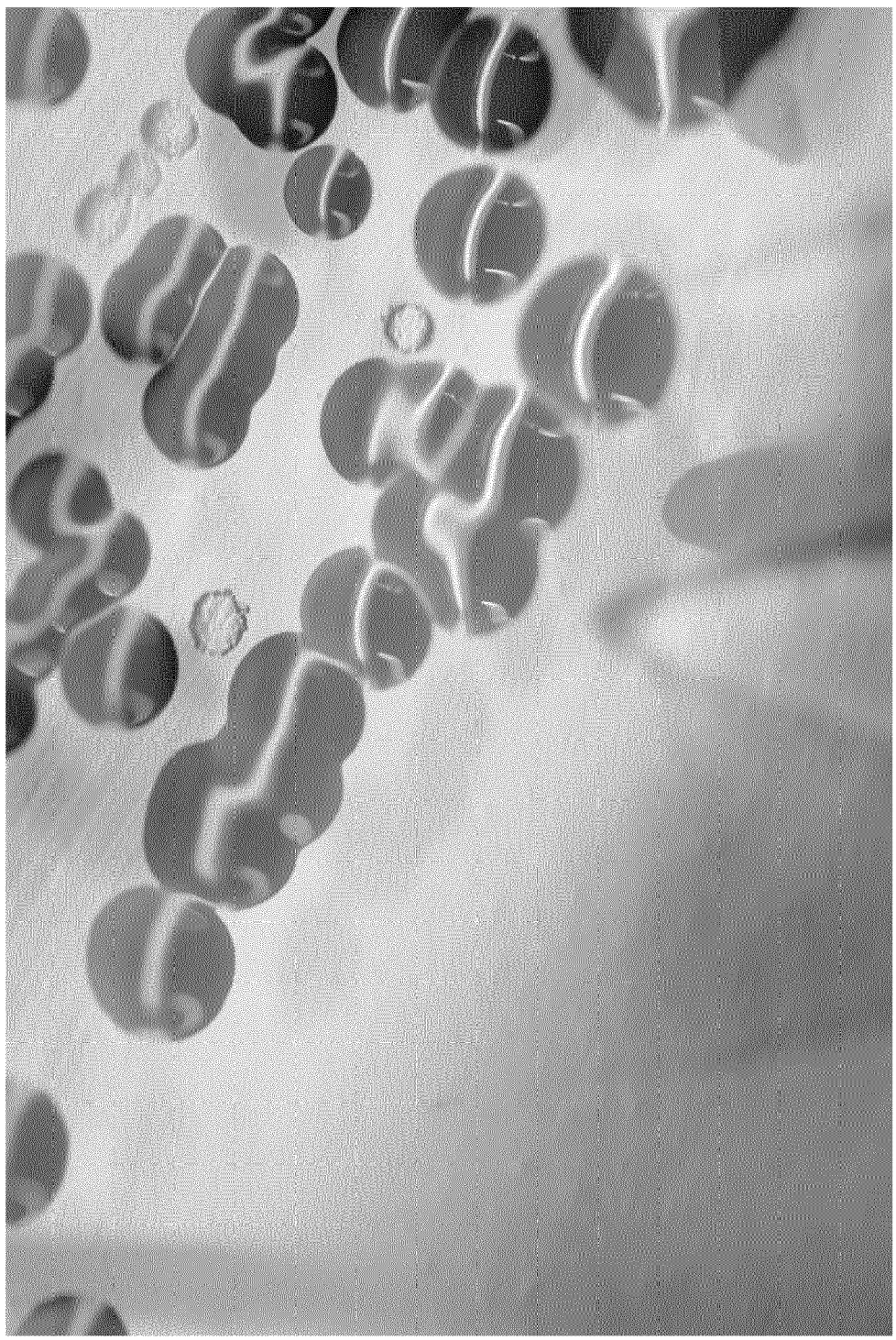
FIG. 34: Five flat, small colonies of *Aliivibrio friggiae* under strong inhibition among *Aliivibrio wodanis* colonies.
Figure 35:
FIG. 35: A dominating number of *Aliivibrio friggiae* colonies (small and flat) inhibited by a lower number of *Aliivibrio wodanis* colonies (large and mucoid).

The bacterium A. friggiae was isolated on blood agar base 2 (Difco) with 5% cattle blood with both 0.9% NaCl and 2.5% NaCl at 8 or 10° C. for 3 to 6 days. A. friggiae grew with pure culture from head-kidney or liver and in mixed culture from ulcers and mostly in mixed culture from the mid-intestine and the anal opening. However, in many salmon that died from friggiosis predominantly pure culture of A. friggiae was detected from the mid-intestine and anus in addition to pure culture from the head-kidney and liver. Also, a dominant growth of *A. friggiae* could be seen from ulcers in some cases. The colonies had a brownish to grey colour and a diameter from pin-point to 3 mm with a convex, round shape, a butyrous consistency and a regular edge (FIGS. 31 and 32). The bacterial cells were Gram-negative bent or straight rods of typical *vibrio*-like appearance of the cells with a size of 0.9-1.3×2-5 µm. Secondary growth occurred at blood agar (5% cattle blood in Blood agar base 2, Difco) with good growth after 3 days at a temperature range from +4 to +15° C. The growth was less rich at +0.9% than at 2.5% NaCl. The colonies were anhemolytic but produced a 2 to 3 mm wide partially haemolytic ring in the blood agar 2 mm away from the colony edge.

*A. friggiae* was often isolated together with other bacteria from the head kidney and liver of Atlantic salmon. The other bacteria from these organs were most often *Aliivibrio wodanis*, but also *Aliivibrio logei* (FIG. 21) and other variants of *Vibrio* bacteria in addition to *Moritella viscose* a minor number of times. From ulcers at various parts of the body the same bacteria as from the inner organs were often isolated in addition to various other bacteria like *Vibrio splendidus*, *Photobacterium phosphoreum*, *Moritella* sp. and rarely *Vibrio tapetis* (when the temperature was above 10° C.), all in low numbers compared to the dominating bacteria in the culture.

A characteristic growth feature was registered on blood agar plates with 0.9% NaCl when *A. friggiae* colonies grew close to colonies of *A. wodanis*. In such situations the growth of *A. friggiae* was dramatically inhibited in a way that gave small, flat, transparent colonies from pin-point size to only 0.5 mm in the vicinity of *A. wodanis* colonies (FIGS. 31, 33, 34 and 35). One single *A. wodanis* colony can express its inhibitory factor that is probably secreted and diffused with a strong inhibitory effect on the growth of *A. friggiae* colonies as far as 10 to 12 mm away from the *A. wodanis* colony. However, the inhibitory effect stops relatively abrupt when the *A. friggiae* colonies are located further away from the *A. wodanis* colonies. In a mixed culture with *A. friggiae* colonies in clear dominance in frequency with only a few colonies of *A. wodanis* compared to more than for instance one hundred *A. friggiae* colonies the *A. friggiae* colonies are inhibited in its growth (FIGS. 31 and 35)). The occurrence of other bacteria in addition to *A. friggiae* and *A. wodanis* in the culture does not seem to impact this clearly dominant activity by *A. wodanis* on *A. friggiae*. There is a similar but differently appearing inhibition by *A. wodanis* against *M. viscosa* and rarely against strains of the same species (*A. wodanis*) but not against other bacteria observed so far.

The clear inhibitory activity by *A. wodanis* against *A. friggiae*, *M. viscosa* and a few strains of *A. wodanis* is not at all observed on blood agar plates with 2.5% NaCl from the same fish sample spread onto the plates with different level of NaCl in parallel. The dominant activity of *A. wodanis* does not seem to be regulated by temperature within the relevant range for occurrence of friggiosis in farmed salmon.

Biochemical tests demonstrated that *A. friggiae* could degrade gelatin and nitrat. The closest species based on the phenotypical tests was *A. wodanis* that degraded tryptophan that *A. friggiae* did not do.

DNA sequence of the 16S rDNA gene gave in BLAST alignment best similarity to different isolates of *A. wodanis* and only one to three basepairs separated the *A. friggiae* from *A. wodanis*. However, the various phenotypical features as colony appearance and hemolysis including the clinical and pathological changes during infection clearly separates *Aliivibrio friggiae* as a separate species different from *Aliivibrio wodanis*.

*Aliivibrio friggiae* 130206K7F2 506 has been deposited at the National Collection of Industrial, Food and Marine Bacteria, Aberdeen, Scotland, United Kingdom and been assigned accession number NCIMB 42181. The isolate is biologically pure.

Growth and Maintenance of *Aliivibrio friggiae*

*Aliivibrio friggiae* grows well on blood agar with 5% cattle blood and on Marine agar (DIFCO) made with natural sea water. It grows strongly on Luria Broth. The growth occurs well at various NaCl concentrations from 0.9% and higher but best at about 2.5% NaCl and at temperatures from about +4° C. or lower to +18° C. with almost equal growth speed up to 12° C. The strain can be stored at −80° C. in Luria Broth added 10% glycerol.

Pathogenic Activity of *Aliivibrio friggiae*

Figure 40:
FIG. 40: Necrosis of the mandibular jaw and mottled bleedings in the liver caused by friggiosis.
Figure 41:
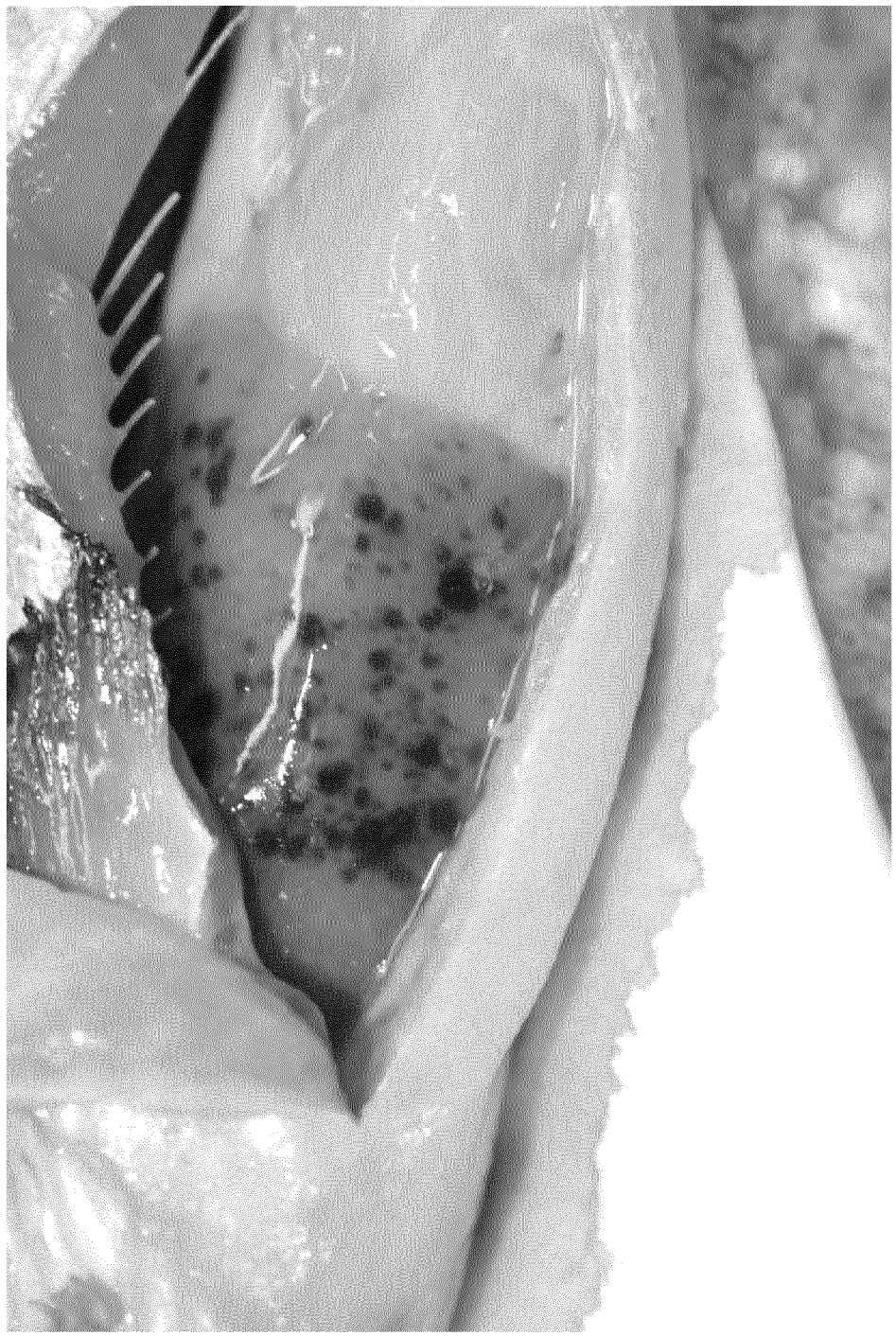
FIG. 41: Mottled bleedings of varying age in the liver in a salmon with chronic friggiosis.
Figure 42:
FIG. 42: Large mottled bleedings in a pale fatty degenerated liver.
Figure 43:
FIG. 43: Transparent ascites liquid coloured weak red by blood in an Atlantic salmon with friggiosis.

Atlantic salmon with friggiosis caused by *Aliivibrio friggiae* suffer from septicaemia with a high number of bacteria in head kidney and liver. The liver in a large part of the friggiosis cases show multiple dark bleedings on the surface from 1 mm to 10 mm in size with sharp demarcation from the rest of the liver surface that is more pale than normal (FIGS. 40, 41 and 42). In addition there are in about 10% of the cases an occurrence of ascites in the abdomen consisting of a transparent light serum coloured colour often with a weak taint of dark red colour from lysed erythrocytes (FIG. 43).

Figure 1:
FIG. 1: Friggiosis with exophtalmus in Atlantic salmon (*Salmo salar* L.).
Figure 2:
FIG. 2: Friggiosis with extended exophtalmus in Atlantic salmon.
Figure 3:
FIG. 3: Eye bulb puncture caused by friggiosis.
Figure 4:
FIG. 4: Eye socket undermined and ulcer development by friggiosis.
Figure 5:
FIG. 5: Loss of eye and ulcer development on the side of the head by friggiosis.
Figure 6:
FIG. 6: Ulcer developed from the tip of mandibula by friggiosis.
Figure 7:
FIG. 7: Extended ulceration of mandibula by friggiosis.
Figure 8:
FIG. 8: Complete ulceration of mandibula by friggiosis.
Figure 9:
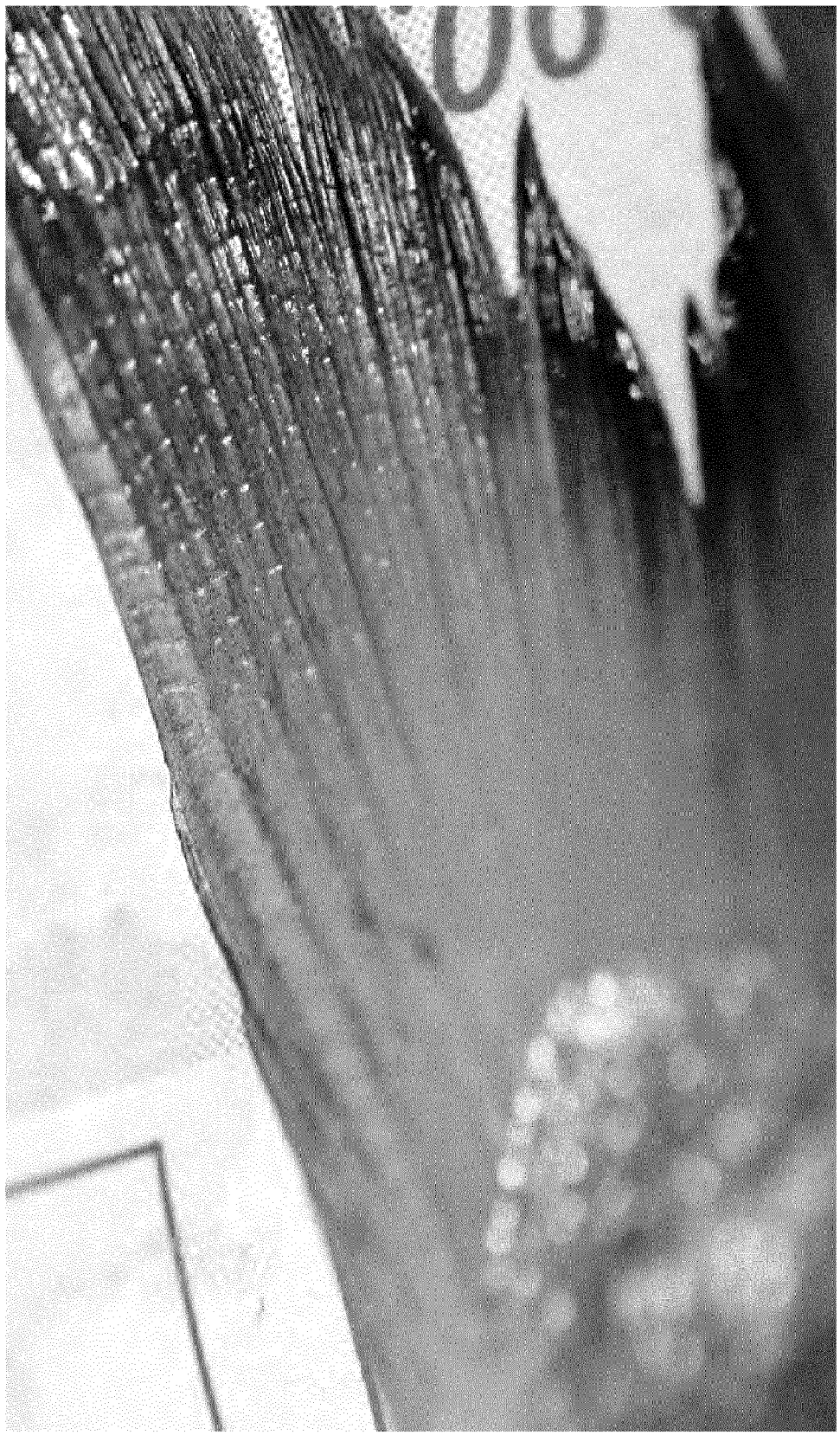
FIG. 9: Stasis in blood vessel of the tail fin indicating strong immune activity.
Figure 10:
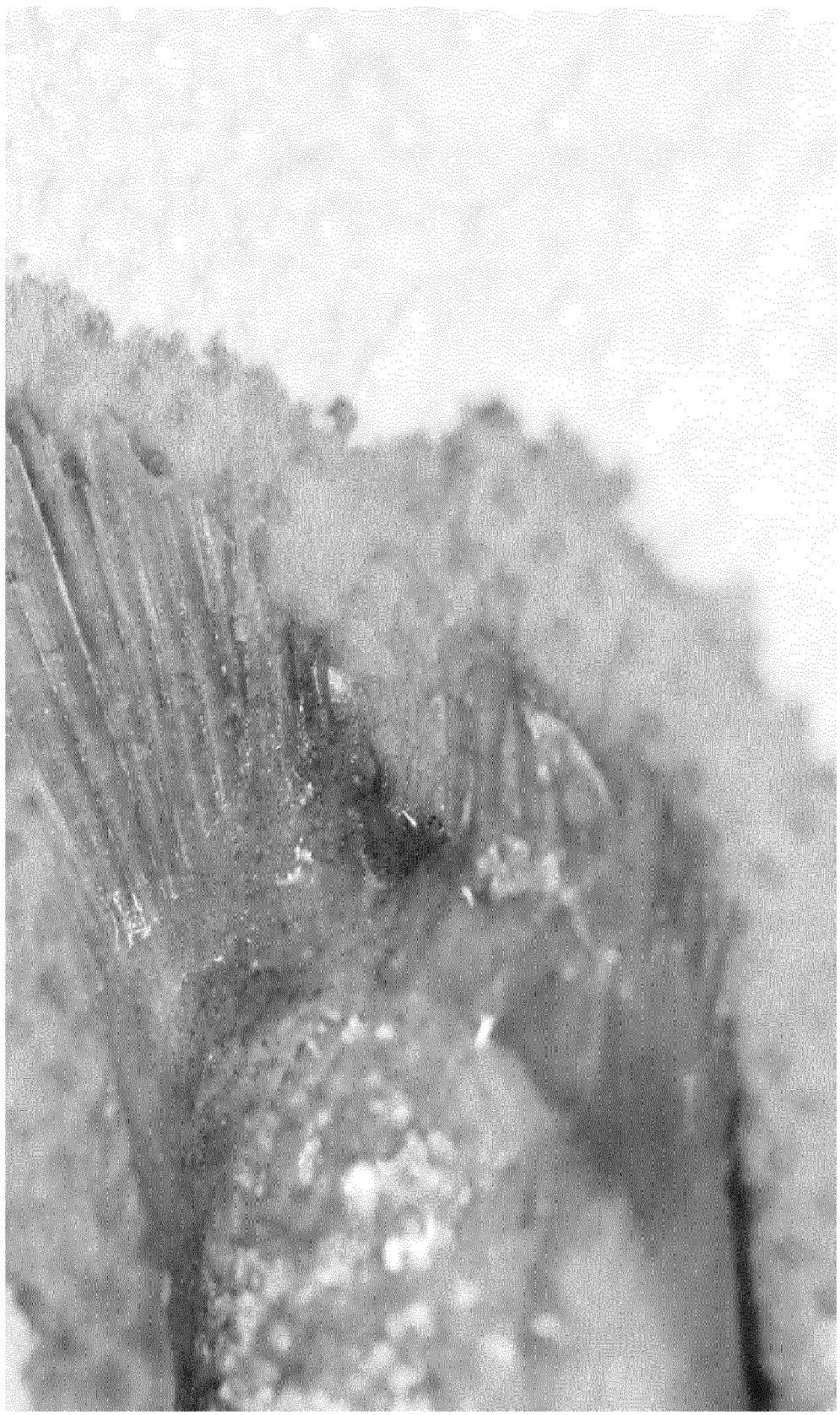
FIG. 10: Heavily necrotic tail fin caused by bizioniosis.
Figure 11:
FIG. 11: Atlantic salmon with extensive fin rot and large skin ulcer covering much of the skin heavily affected by bizioniosis.
Figure 12:
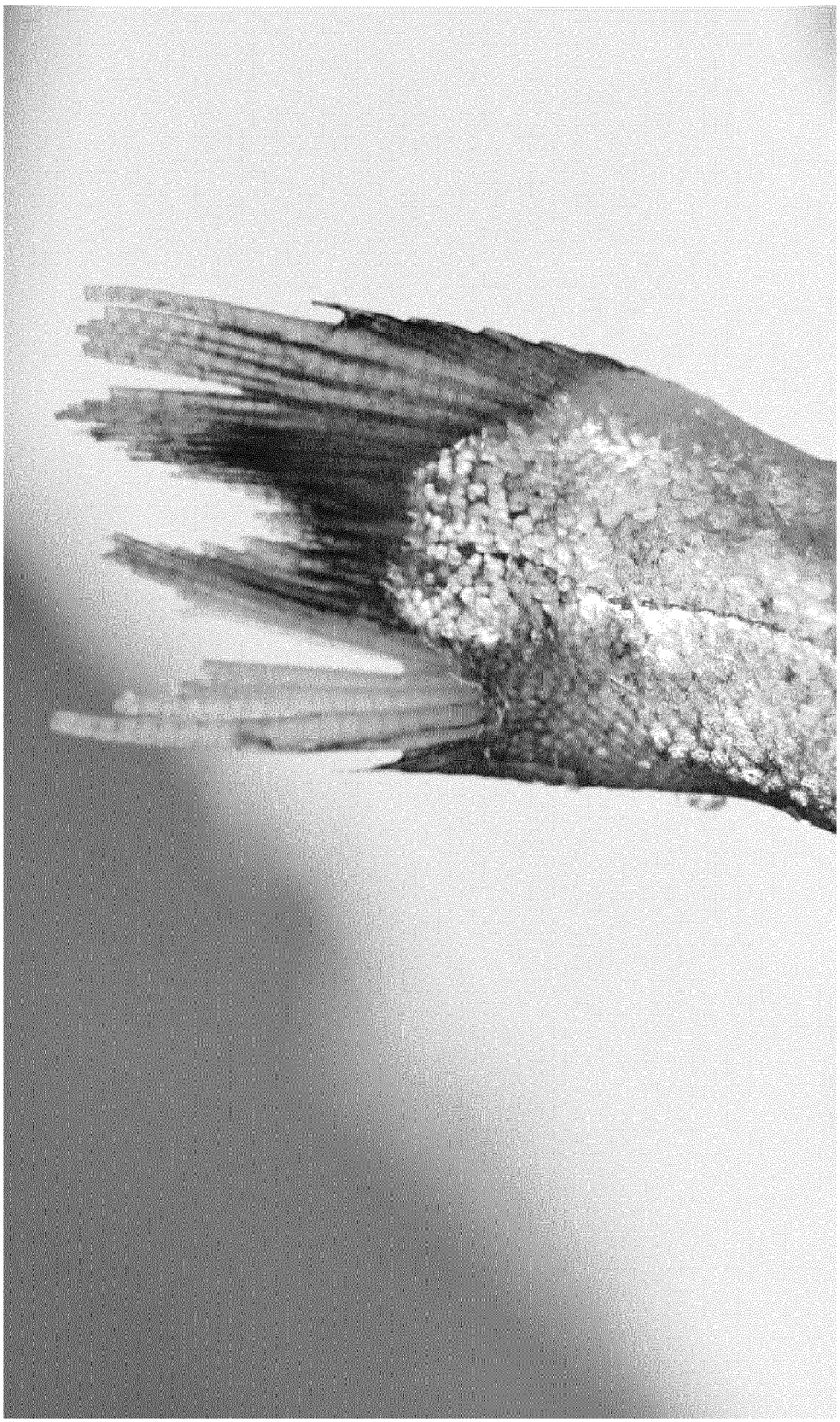
FIG. 12: Pale necrotic areas of the tail fin caused by bizioniosis.
Figure 13:
FIG. 13: Necrotic outer areas of the tail fin caused by bizioniosis.
Figure 14:
FIG. 14: Almost lost tail fin by necrosis caused by bizioniosis leaving characteristic fin profile in the mid-fin.
Figure 15:
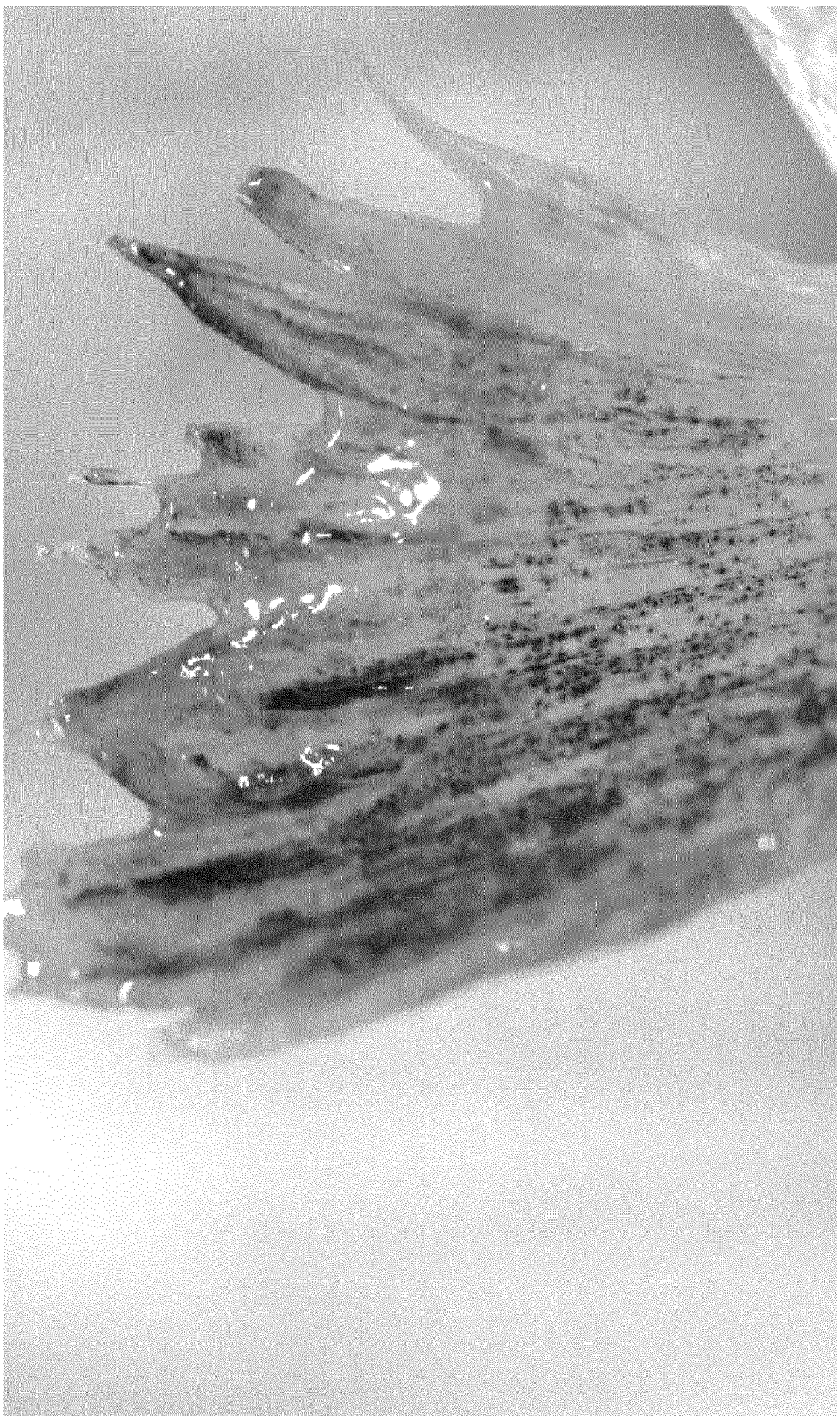
FIG. 15: Hemostasis in the arterioles of the pectoral fin.
Figure 16:
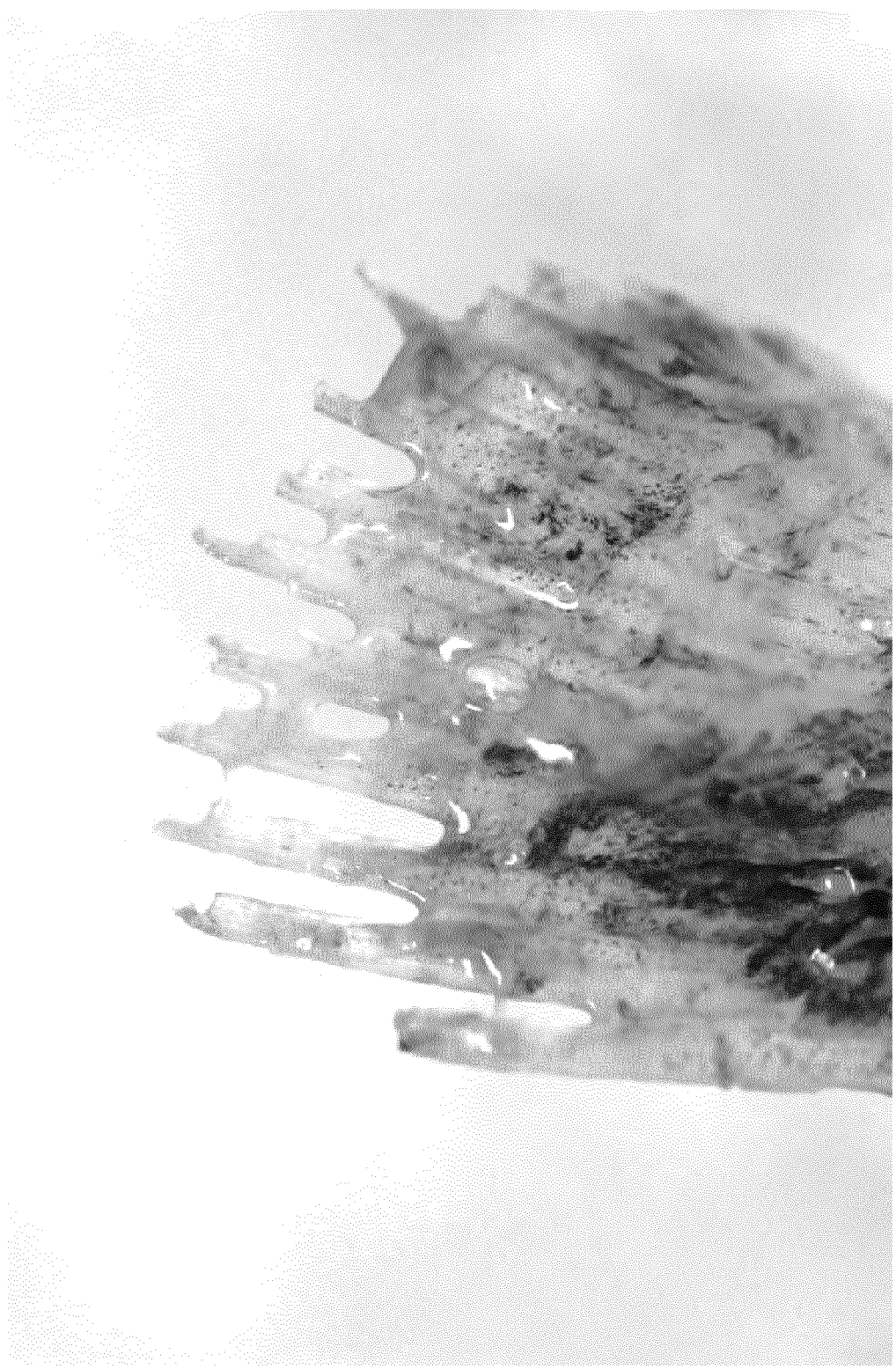
FIG. 16: Necrosis of the pectoral fin margin caused by bizioniosis.
Figure 17:
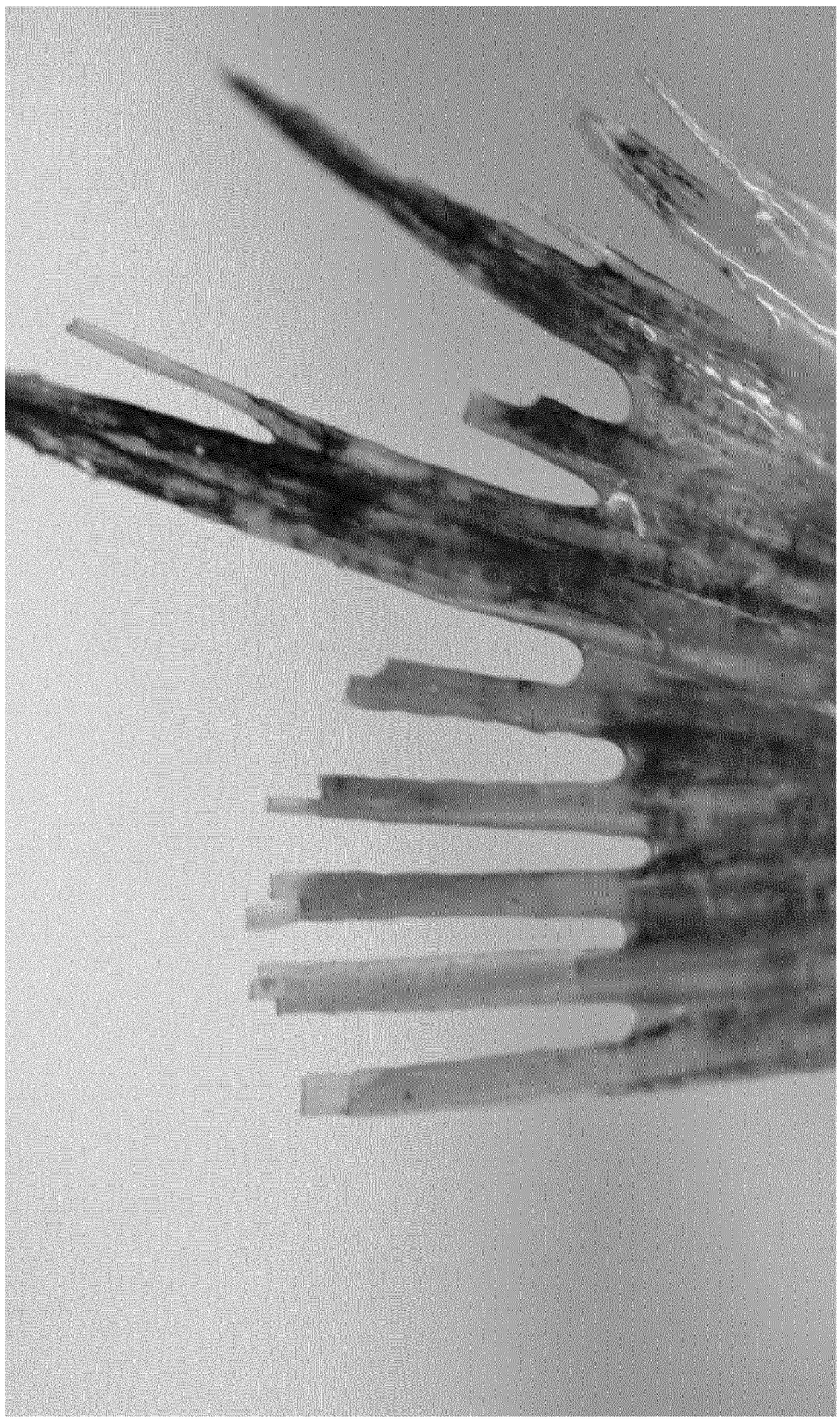
FIG. 17: Necrosis of pectoral fin also including bone rays caused by bizioniosis.
Figure 18:
FIG. 18: Near complete necrosis of the pectoral fin rays and the inter-located soft tissue caused by bizioniosis.
Figure 19:
FIG. 19: Necrotic pectoral fin have caused ulcer in the skin of the abdominal wall.
Figure 20:
FIG. 20: Ulcers behind both pectoral fins with perforation of the abdominal wall on both sides.
Figure 21:
FIG. 21: Ulcer behind the necrotic pectoral fin has perforated the abdominal wall and exposed internal organs while living.
Figure 22:
FIG. 22: Fish from the same tank with bizioniosis ("smolt syndrome") with mass occurrence of ulcer behind the pectoral fins contributed by the active motion of the pectoral fins with eroded rays.
Figure 23:
FIG. 23: Massive tail fin rot in a tank with bizioniosis.
Figure 24:
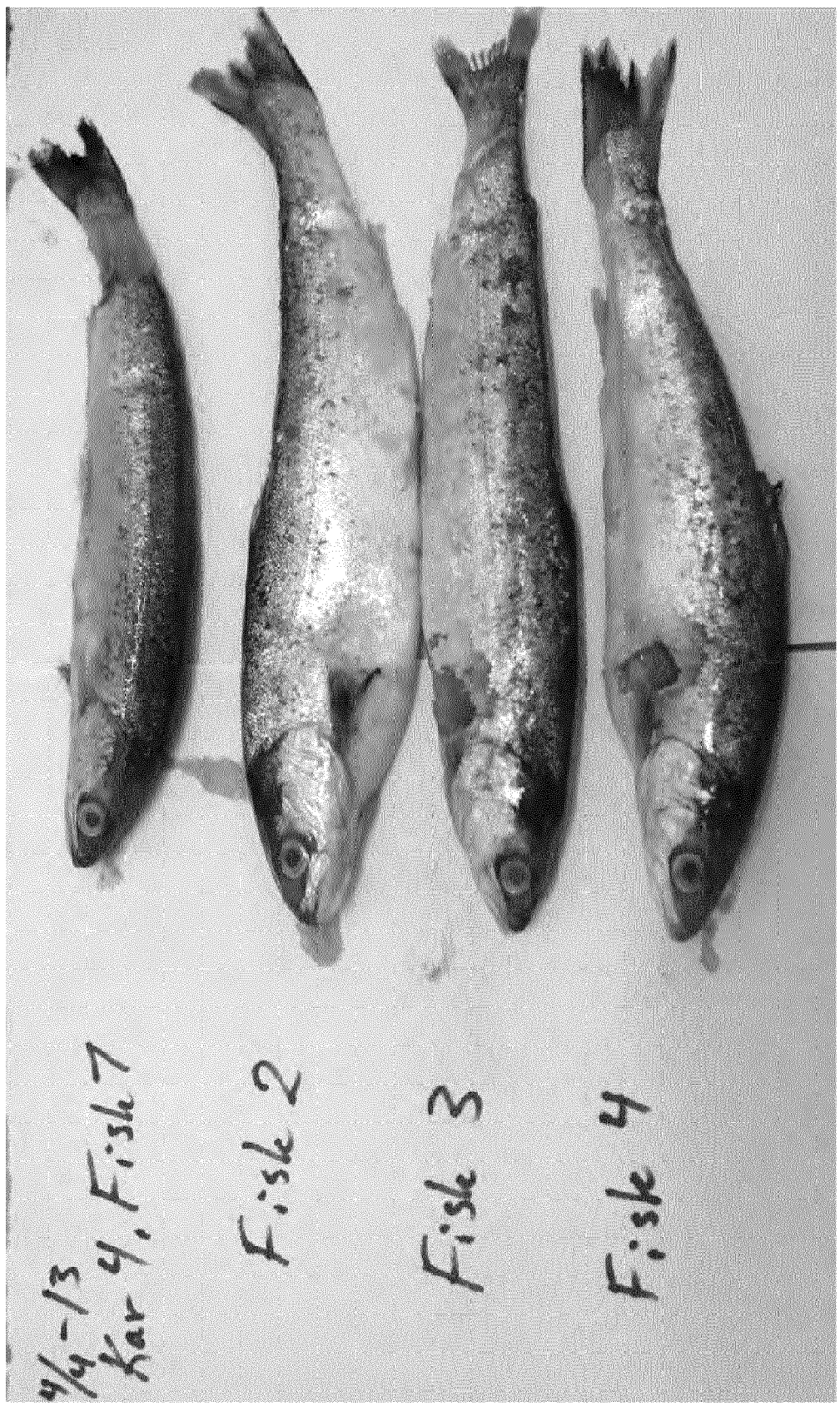
FIG. 24: Four salmon smolts with different typical changes caused by *Bizionia piscinecroseptica* and parallelly infected by *Aliivibrio wodanis*.
Figure 25:
FIG. 25: Skin ulcers have a clear tendency to occur predominantly behind the pectoral fins during an acute outbreak of bizioniose and the ulcers are invaded by both *B. piscinecroseptica* and *A. wodanis* normally.
Figure 26:
FIGS. 26 and 27: Tail- and fin rot in addition to ulcers behind the pectoral fins is the typical visible sign of acute bizioniose.
Figure 27:
Figure 28:
FIG. 28: Tail and fin rot that have extended into the tail leaving the rear columna exposed.
Figure 29:
FIGS. 29, 30 and 36: Characteristic skin ulcers occurring in both wodanosis, caused by *A. wodanis*, winter ulcer caused by *Moritella viscosa*, friggiose caused by *Aliivibrio friggiae* and in bizioniosis often with more than one pathogen operating coordinated in the ulcer development.
Figure 30:
Figure 36:
Figure 37:
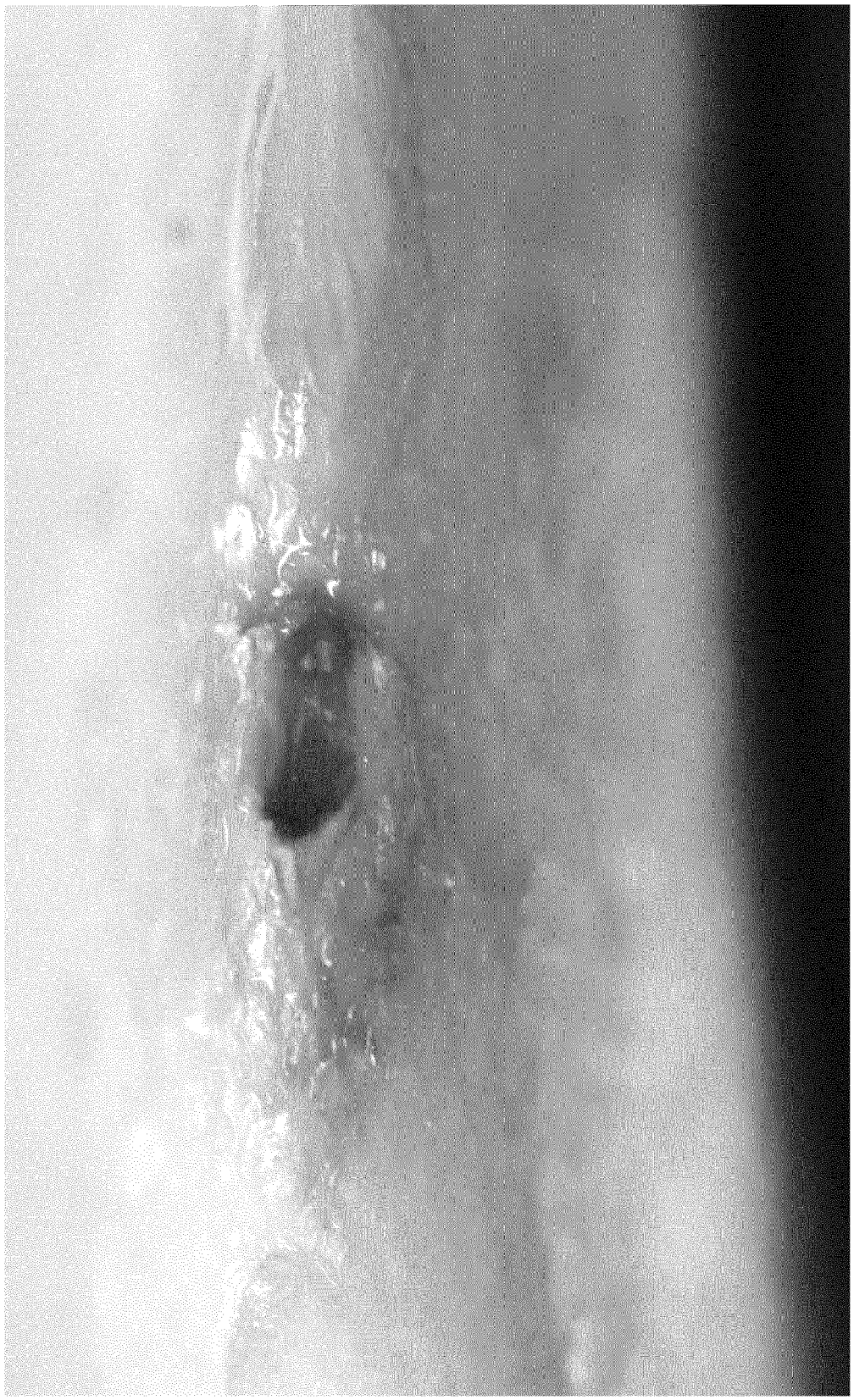
FIG. 37: Redness surrounding the vent indicating infection and inflammation caused by infection.
Figure 38:
FIGS. 38: and 39: Ulcer surrounding the anal opening.
Figure 39:
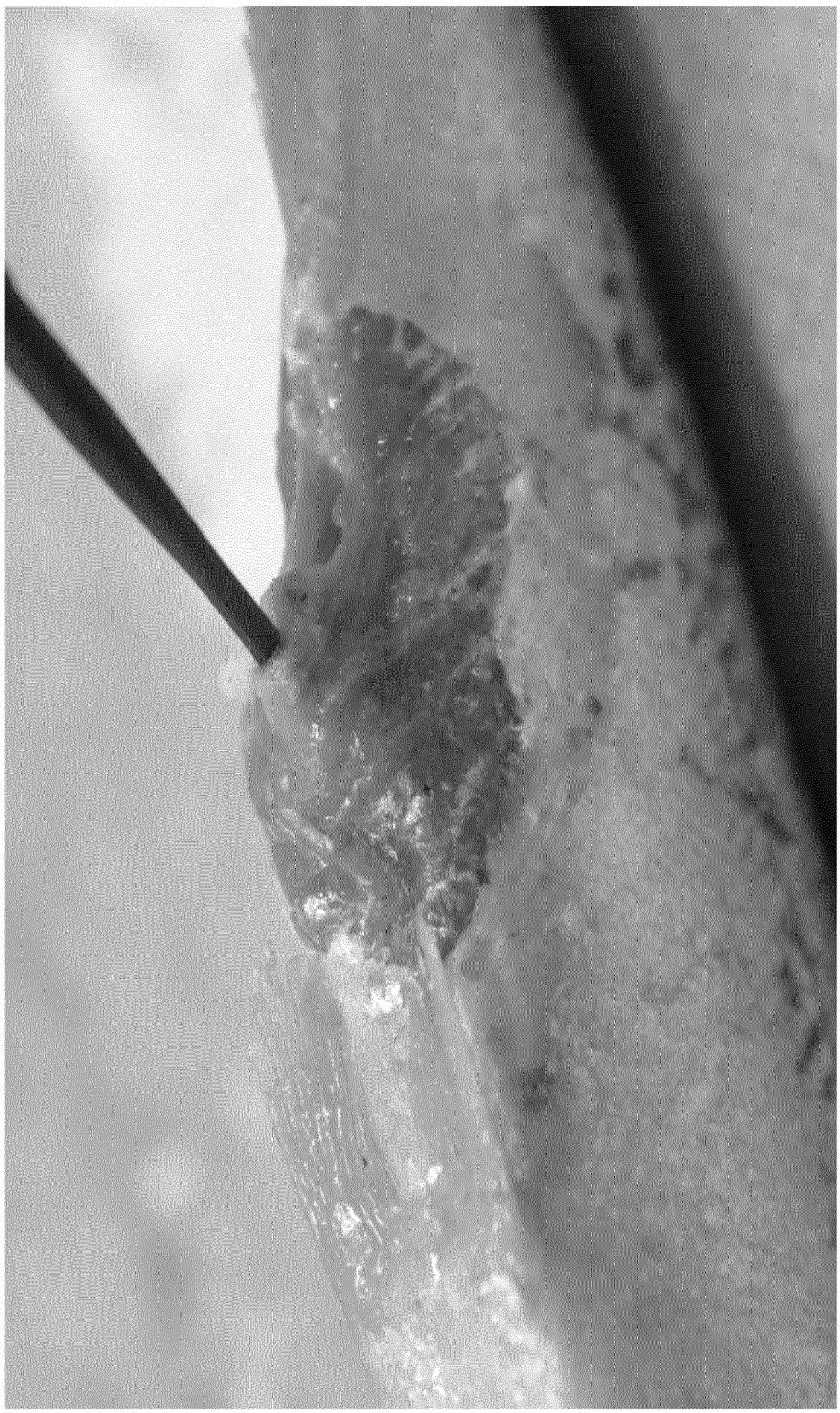

*A. friggiae* is often causing ulcers in the same areas of the fish surface as *A. wodanis* and *M. viscose* i.e. behind the pectoral fins (FIGS. 19, 20, 21 and 22) or spread out on the body in a number from one large ulcer of typically 30 millimeter in diameter to often 3 to 4 ulcers of similar size (FIGS. 29, 30 and 36). Often *A. friggiae* causes infection of the eye bulb directly through cornea with puncture of the eye as a result (FIGS. 3 and 5). As *A. wodanis*, *A. friggiae* can undermine the eye socket and press the eye out causing marked exophtalmus because of edema and inflammation (FIGS. 1, 2, 4 and 5). In addition *A. friggiae* can participate in an infection of the tip of the mandibula and less often the tip of the maxilla (FIGS. 6, 7 and 8). Many of the ulcers and internal infected organs present *A. friggiae* in a mixed infection with *A. wodanis* (FIGS. 32, 33, 34 and 35). However, mixed infection may occur with *A. friggiae* and other *Aliivibrio* bacteria as *Aliivibrio salmonicida* and *Aliivibrio logei* (FIG. 32) as revealed by agar culture.

Friggiosis causes a relatively low number of mortalities in the population but there may be periods of an increased numbers of dead fish occurring and the increase and decline of the outbreak is not abrupt and may change over many days and weeks. In a population with friggiosis the disease seems to go on for many months but often at a low intensity and it often starts when the salmon has been in the sea for several months (FIG. 44).

The source of *A. friggiae* may be the intestinal microbiota of the salmon since in most cases of friggiosis there is a parallel growth and dominant occurrence of *A. friggiae* in the whole length of the intestine. In such changes of the intestinal flora it is plausible that *A. friggiae* passes the intestinal wall and enters the blood circulation. Also in the microbiota *A. wodanis* may dominate the microbiota together with *A. friggiae*. It seems that *A. logei* is the most common member of a healthy intestinal microbiota.

In the long experiments with Atlantic salmon exposed to natural sea-water for more than one year it appears that close to 20% of the salmon that die from infection may have friggiosis as the only or dominant disease FIG. 44). However, *A. friggiae* may often be seen in low numbers in ulcers or organs when *A. wodanis* is dominating the diseased salmon with wodanosis in particular it may be found as a substantial part of the intestinal microbiota often together with *A. wodanis* during wodanosis.

The invention will be further described in the following examples, which do not limit the scope of the invention described in the claims

EXPERIMENTAL SECTION

1. *Bizionia* sp 1.1 Experimental Design

Atlantic salmon smolts (40 gram) were challenged with *Bizionia* sp. 130524K2F7 intraperitoneally (7 individuals), by bath in 35 minutes (8 individuals), intraperitoneally with a mixture of *Bizionia* sp. 130524K2F7 and *Aliivibrio friggiae* 130206K7F2 506 (1 individual) and with only *Aliivibrio friggiae* 130206K7F2 506 (5 individuals). In addition 3 smolts were not challenged artificially. Those 24 smolts were left into a tank with goldsinny wrasse.

The surviving goldsinny wrasse individuals from the experimental vaccination referred to previously were bath-challenged with *Bizionia* sp. 130524K2F7 for 35 minutes, 18 were challenged intraperitoneally with *Bizionia* sp. 130524K2F7 and 12 were not challenged.

*Bizionia* sp. 130524K2F7 cultured at 10° C. from the frozen stock culture at −80° C. in Luria Broth with 2.5% NaCl were heat inactivated at 37° C. overnight and spun down and diluted and washed in PBS before addition of Freund's incomplete adjuvant (FICA) and glucan (40/60 volume/volume ratio). The *Bizionia* sp. antigen was mixed with several other heat inactivated bacteria into an experimental vaccine. Experimental control vaccines without the *Bizionia* sp. 130524K2F7 antigen were prepared. The experimental vaccines were cultured to control no viability of the heat-inactivated bacterial cells.

Atlantic salmon smolts (60 to 150 gram) in groups of 50 individuals and in four identical tanks were injected intraperitoneally with 0.1 ml of each experimental vaccine in the same manner as performed in commercial Atlantic salmon farms after a bath in an anaesthetic solution of 0.005% benzocain for an optimal anaestesiae to develop. A commercially used vaccine for Atlantic salmon was included in a control group in 3 of the four tanks. In total 200 smolts were vaccinated with the experimental vaccine containing *Bizionia* sp. 130524K2F7 antigen. In total 1300 Atlantic salmon smolts were vaccinated with various experimental vaccines in 5 tanks of 1400 liters. Natural sea water from 70 meter depth in the Oslofjord (Solbergstrand) were supplied to the tanks at 1200 liters per hour. The temperature of the sea water varied from +7° C. when the experiment started to 8.5° C. after 5 months duration of the experiment.

Since "bizioniosis" developed heavily in all tanks from day 4 after sea-launch, freshwater of the same temperature was added to a salinity of 2% to reduce the early loss of a major part of the population in the unprotected groups. After 4 weeks full sea water was supplied to one tank, then every second week full sea-water was supplied to another of the remaining tanks on brackish water.

250 wild-caught goldsinny wrasse of 10 to 30 gram was intraperitoneally similarly vaccinated with 0.1 ml of the same experimental vaccines as the Atlantic salmon after bath anaesthesia in 0.005% benzokain. Half of the goldsinny wrasse got the vaccine deposited in the abdomen and half in the swim bladder. The goldsinny wrasse was kept in the same tank and a group of 60 fish were vaccinated with *Bizionia* sp. 130524K2F7 antigen. Commercial vaccine for Atlantic salmon was not included in the vaccine experiment with goldsinny wrasse. The goldsinny wrasse individuals were kept in the same type of 1400 liters tank as Atlantic salmon and with the same water quality.

1.2 Results from Challenge Study of Unvaccinated Smolts

From one to six days after the challenge with *Bizionia piscinecroseptica* 130524K2F7 all unvaccinated Atlantic salmon smolts died from "bizioniosis" as verified by Gram-staining of kidney smears and cultivation of secondary pathogens. The smolts died at a time after challenge that had no relation to form of challenge.

Only two goldsinny wrasse died on day 5 and 7 after the challenge.

1.3 Result of Experimental Vaccination and Natural Challenge

An outbreak of "bizioniosis" started in both the Atlantic salmon tanks and in the goldsinny tank 4 days after vaccination. The intensity of the outbreaks varied from heavy (8% daily loss) to barely occurring in the 6 tanks involved.

The vaccine with *Bizionia piscinecroseptica* 130524K2F7 antigen protected the 100% of the goldsinny wrasse after 4 days when the outbreak started. The vaccinated Atlantic salmon was fully (99%) protected against "bizioniosis" 6 days after vaccination. The vaccine protected both fish species fully the first month after vaccination including the stay in brackish water. In the following months "bizioniosis" outbreaks occurred regularly with a top of disease after transfer of the Atlantic salmon from brackish to full sea-water. The period with brackish water terminated the infection in the tanks. The vaccine with *Bizionia piscinecroseptica* 130524K2F7 antigen protected well after 5 months in sea, but single individuals died from infection with wodanosis, cold water vibriosis and vibriosis because *V. logei* was included as antigen in the vaccine with *Bizionia piscinecroseptica* 130524K2F7 antigen.

As demonstrated herein vaccination against "bizioniosis" is highly effective and produces an extremely early protection; in less than one week in Atlantic salmon compared to 8 weeks that is currently considered as optimal time for immunity to develop at a water temperature of 8° C. *Bizionia piscinecroseptica* and/or other species of the genus *Bizionia* and/or antigens thereof should therefore be a major key component of a fully protective new generation vaccine that contains multiple bacterial pathogens responsible for the major part of the loss of Atlantic salmon in the sea part of the production cycle in aquaculture. For protection of Atlantic salmon the first 1 to 1.5 months in the sea, the *Bizionia piscinecroseptica* antigen is without doubt the most important antigen. However, "bizioniosis" develops in a concerted action with other infections like wodanosis, winter ulcer, friggiosis, cold water vibriosis and vibriosis, and preferably all the causative agents causing these diseases should be included to fully protect the Atlantic salmon also in the first weeks in the sea. Also *Aeromonas salmonicida* ss *salmonicida* is an important component as it has been involved in the commercial vaccines together with *Aliivibrio salmonicida* and *Vibrio anguillarum*. Also bacteria such as *Tenacibaculum* sp, such as *Tenacibaculum maritimum*, *Flavobacterium*, such as *Flavobacterium psychrophilum* and *Flavobacterium columnare*, *Aliivibrio friggiae* and *Vibrio anguillarum* could be included in a vaccine as further discussed elsewhere herein.

It seems like *Bizionia* sp. almost regularly "opens" the fish directly and indirectly for infections with the other bacterial pathogens (and possibly viruses) through more or less extensive tail and fin rot.

2. Aliivibrio friggiae

2.1 Challenge Experiments with Aliivibrio friggiae

Aliivibrio friggiae has been challenged intraperitoneally with high numbers of bacterial cells without causing friggiosis.

One of the tanks with Atlantic salmon that were part of the vaccine experiment started at Solbergstrand 1. Jul. 2012 had low mortality caused by friggiosis starting 5 months from vaccination after an early period with tail- and fin-rot and wodanosis. Three weeks after bath challenge (immersion) in marine water with a concentration of approximately $10^7$ cfu added for one hour there were no sign of friggiosis or any other disease for 4 weeks and 4 days. However from one month after immersion challenge and for more than four months it was a long chronic outbreak in all vaccination groups of the population in the tank with an average loss of 0.7% of the population daily. In addition, pulses of small outbreaks of wodanosis occurred in this population during those four months. In the other parallel tanks there were also mortalities caused by friggiosis in the same period but clearly in a lower frequency and more singly diseased individuals.

2.2 Vaccination

Aliivibrio friggiae (Aliivibrio friggiae 130206K7F2 506) was included in a vaccination experiment that started in March 2013 and in a vaccination experiment started in June 2013. The experimental vaccines involved were complicated consisting of various bacteria including A. wodanis and M. viscose and for the June 2013 experiment the novel Bizionia piscinecroseptica 130524K2F7 (deposition number NCIMB 42185) bacterium was included. However, after 4 months the number of cases with friggiosis dropped to virtually zero in all vaccination groups including the negative control indicating a low transmission frequency of A. friggiae because of many immune protected animals in the total population (FIGS. 44, 45, 46, 47, 48 and 49). This epidemiology is clearly different from the continuous occurrence of friggiosis in the first vaccine experiment that lasted for 15 months mimicking the full production cycle in the Atlantic salmon farms (FIG. 44).

In the population of tank "Kar SA" there is a peracute "smolt syndrome" the first 2 weeks after sea-launch. The vaccine with Bizionia piscinecroseptica clearly protected against the acute "smolt syndrome" while the vaccines with a rich oil-based adjuvant like FICA or the adjuvant in the commercial vaccine increased the mortality clearly compared to the negative control. It can also be seen that extra antigens from for instance A. friggiae seems to protect the fish in this tank the first two weeks after sea-launch.

In tank "Kar S4" there was a less peracute outbreak of the "smolt syndrome" and it was occurring actively in the tank the first month after sea-launch. In this period A. friggiae had no observed role in the infections in this tank in opposite to what was the case in tank "Kar SA". However, A. wodanis produced many infections and killed a substantial number of the salmon in addition to Bizionia pisciseptonecrotica. The last vaccine generation with B. piscinecroseptica antigens in addition to the others seemed to protect the salmon very well the first month in the sea in this tank.

In tank "Kar S5" A. friggiae was causing friggiose as the dominating disease the first month in the sea. Both vaccines with A. friggiae antigens protected the fish well during the first month in sea. It is also very important to note that the non-vaccinated control seemed to be relatively well protected against friggiosis indicating the vaccine administration itself increases the risk of occurrence of friggiosis outbreaks. It is clear that in this experiment the commercial vaccine stimulated to occurrence of friggiose compared to the other vaccines.

In tank "Kar S4" an outbreak of classical winter ulcer with a major contribution of Moritella viscose occurred after full sea-launch for the second time after the period in brackish water. In this situation non-vaccinated salmon had a high mortality risk as was also the case with the vaccine group of with the second vaccine generation. The reason for this is a possible antagonistic effect from the inclusion of V. logei antigens into the vaccine. The various observations seem to support that V. logei has a more protective role in the intestinal flora than being a potential pathogen.

In tank "Kar S5" there was no disease outbreak after the first three weeks in marine water.

All diseased and dead salmon from all vaccination experiments were autopsied and close to 3000 individual salmons have been investigated by autopsy, histopathology, culture and Gram-staining of smears from ulcers and kidney and sometimes liver.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Unless expressly described to the contrary, each of the preferred features described herein can be used in combination with any and all of the other herein described preferred features.

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

Norwegian School of Veterinary Science
Post Box 8146 Dep
0033 Oslo
Norway

VIABILITY STATEMENT
issued pursuant to Rule 10.2 by the
INTERNATIONAL DEPOSITARY AUTHORITY
identified on the following page

NAME AND ADDRESS OF THE PARTY
TO WHOM THE VIABILITY STATEMENT
IS ISSUED

| I. DEPOSITOR | II. IDENTIFICATION OF THE MICROORGANISM |
|---|---|
| Name: AS ABOVE  Address: | Accession number given by the INTERNATIONAL DEPOSITARY AUTHORITY:  NCIMB 42181  Date of the deposit or of the transfer[1]:  24 October 2013 |

III. VIABILITY STATEMENT

The viability of the microorganism identified under II above was tested on 28 October 2013[2]. On that date, the said microorganism was:

[X] viable[3]

[ ] no longer viable[3]

[1] Indicate the date of the original deposit or, where a new deposit or a transfer has been made, the most recent relevant date (date of the new deposit or date of the transfer).

[2] In the cases referred to in Rule 10.2(a)(ii) and (iii), refer to the most recent viability test.

[3] Mark with a cross the applicable box.

Form BP/9 (first page)

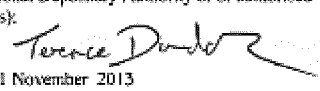

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

Norwegian School of Veterinary Science
Post Box 8146 Dep
0033 Oslo
Norway

VIABILITY STATEMENT
issued pursuant to Rule 10.2 by the
INTERNATIONAL DEPOSITARY AUTHORITY
identified on the following page

NAME AND ADDRESS OF THE PARTY
TO WHOM THE VIABILITY STATEMENT
IS ISSUED

| I. DEPOSITOR | II. IDENTIFICATION OF THE MICROORGANISM |
|---|---|
| Name: AS ABOVE | Accession number given by the INTERNATIONAL DEPOSITARY AUTHORITY: |
| Address: | NCIMB 42183 |
| | Date of the deposit or of the transfer[1]: |
| | 24 October 2013 |

III. VIABILITY STATEMENT

The viability of the microorganism identified under II above was tested on 28 October 2013[2]. On that date, the said microorganism was:

[X][3] viable

[ ] no longer viable

[1] Indicate the date of the original deposit or, where a new deposit or a transfer has been made, the most recent relevant date (date of the new deposit or date of the transfer).

[2] In the cases referred to in Rule 10.2(a)(ii) and (iii), refer to the most recent viability test.

[3] Mark with a cross the applicable box.

Form BP/9 (first page)

Form BP/9 (second and last page)

**BUDAPEST TREATY ON THE INTERNATIONAL
RECOGNITION OF THE DEPOSIT OF MICROORGANISMS
FOR THE PURPOSES OF PATENT PROCEDURE**

Norwegian School of Veterinary Science
Post Box 8146 Dep
0033 Oslo
Norway

INTERNATIONAL FORM

VIABILITY STATEMENT
issued pursuant to Rule 10.2 by the
INTERNATIONAL DEPOSITARY AUTHORITY
identified on the following page

NAME AND ADDRESS OF THE PARTY
TO WHOM THE VIABILITY STATEMENT
IS ISSUED

| I. DEPOSITOR | II. IDENTIFICATION OF THE MICROORGANISM |
|---|---|
| Name: AS ABOVE | Accession number given by the INTERNATIONAL DEPOSITARY AUTHORITY: |
| Address: | NCIMB 42121 |
| | Date of the deposit or of the transfer[1]: |
| | 7 March 2013 |

III. VIABILITY STATEMENT

The viability of the microorganism identified under II above was tested on 12 March 2013[2]. On that date, the said microorganism was:

[X] viable

[ ] no longer viable

[1] Indicate the date of the original deposit or, where a new deposit or a transfer has been made, the most recent relevant date (date of the new deposit or date of the transfer).

[2] In the cases referred to in Rule 10.2(a)(ii) and (iii), refer to the most recent viability test.

[3] Mark with a cross the applicable box.

Form BP/9 (first page)

| IV. | CONDITIONS UNDER WHICH THE VIABILITY TEST HAS BEEN PERFORMED[4] |
|---|---|

| V. | INTERNATIONAL DEPOSITARY AUTHORITY | |
|---|---|---|
| Name: NCIMB Ltd.,<br><br>Address: Ferguson Buildng, Craibstone Estate,<br>Bucksburn, Aberdeen,<br>AB21 9YA,<br>Scotland. | Signature(s) of person(s) having the power to represent the International Depositary Authority or of authorised official(s):<br><br>*Terence Dando*<br>Date: 22 March 2013 |

[4] Fill in if the information has been requested and if the results of the test were negative.

Form BP/9 (second and last page)

BUDAPEST TREATY ON THE INTERNATIONAL
RECOGNITION OF THE DEPOSIT OF MICROORGANISMS
FOR THE PURPOSES OF PATENT PROCEDURE

| Norwegian School of Veterinary Science<br>Post Box 8146 Dep<br>0033 Oslo<br>Norway | INTERNATIONAL FORM<br><br>RECEIPT IN THE CASE OF AN ORIGINAL DEPOSIT<br>issued pursuant to Rule 7.1 by the<br>INTERNATIONAL DEPOSITARY AUTHORITY<br>identified at the bottom of this page |
|---|---|

NAME AND ADDRESS OF DEPOSITOR

| I. IDENTIFICATION OF THE MICROORGANISM | |
|---|---|
| Identification reference given by the DEPOSITOR: | Accession number given by the INTERNATIONAL DEPOSITARY AUTHORITY: |
| *Moritella viscosa* 06/09/139 – Ft 5427 | NCIMB 42122 |

| II. SCIENTIFIC DESCRIPTION AND/OR PROPOSED TAXONOMIC DESIGNATION |
|---|
| The microorganism identified under I above was accompanied by:<br><br>[ ] a scientific description<br><br>[X] a proposed taxonomic designation<br><br>(Mark with a cross where applicable) |

| III. RECEIPT AND ACCEPTANCE |
|---|
| This International Depositary Authority accepts the microorganism identified under I above, which was received by it on 7 March 2013 (date of the original deposit)[1] |

| IV. RECEIPT OF REQUEST FOR CONVERSION |
|---|
| The microorganism identified under I above was received by this International Depositary Authority on (date of the original deposit) and a request to convert the original deposit to a deposit under the Budapest Treaty was received by it on (date of receipt of request for conversion) |

| V. INTERNATIONAL DEPOSITARY AUTHORITY | |
|---|---|
| Name: NCIMB Ltd.,<br><br>Address: Ferguson Building, Craibstone Estate<br>Bucksburn, Aberdeen,<br>AB21 9YA,<br>Scotland. | Signature(s) of person(s) having the power to represent the International Depositary Authority or of authorised official(s):<br><br>*Terence Donde*<br><br>Date: 22 March 2013 |

[1] Where Rule 6/4(d) applies, such date is the date on which the status of International Depositary Authority was acquired.

Form BP/4 (sole page)

BUDAPEST TREATY ON THE INTERNATIONAL
RECOGNITION OF THE DEPOSIT OF MICROORGANISMS
FOR THE PURPOSES OF PATENT PROCEDURE

Norwegian School of Veterinary Science
Post Box 8146 Dep
0033 Oslo
Norway

INTERNATIONAL FORM

VIABILITY STATEMENT
issued pursuant to Rule 10.2 by the
INTERNATIONAL DEPOSITARY AUTHORITY
identified on the following page

NAME AND ADDRESS OF THE PARTY
TO WHOM THE VIABILITY STATEMENT
IS ISSUED

| I. DEPOSITOR | II. IDENTIFICATION OF THE MICROORGANISM |
|---|---|
| Name: AS ABOVE | Accession number given by the INTERNATIONAL DEPOSITARY AUTHORITY: |
| Address: | NCIMB 42122 |
| | Date of the deposit or of the transfer[1]: |
| | 5 March 2013 |

| III. VIABILITY STATEMENT |
|---|
| The viability of the microorganism identified under II above was tested on 12 March 2013[2]. On that date, the said microorganism was: |
| [X] viable |
| [ ] no longer viable |

[1] Indicate the date of the original deposit or, where a new deposit or a transfer has been made, the most recent relevant date (date of the new deposit or date of the transfer).

[2] In the cases referred to in Rule 10.2(a)(ii) and (iii), refer to the most recent viability test.

[3] Mark with a cross the applicable box.

Form BP/9 (first page)

REFERENCES

1. Bruno et al. 1998, Gudmundsdottir et al. 2006, Whitman et al. 2000.
2. Aunsmo A, Bruheim T, Sandberg M, Skjerve E, Romstad S, Larssen R B. 2008. Methods for investigating patterns of mortality and quantifying cause-specific mortality in sea-farmed Atlantic salmon *Salmo salar*. Dis Aquat Organ. 2008 Aug. 27; 81(2):99-107.
3. Arnfinn Aunsmo 2009 dissertation Ph.D. thesis, "Health related losses in sea farmed Atlantic salmon—quantification, risk factors and economic impact", at the Norwegian School of Veterinary Science Please provide! (ISBN 978-82-7725-168-4, h.) (Aunsmo et al. 2008)
4. Bowman et al. 2005. Novel members of the family Flavobacteriaceae from Antarctic maritime habitats including *Subsaximicrobium wynnwilliamsii* gen. nov., sp. nov., *Subsaximicrobium saxinquilinus* sp. nov., *Subsaxibacter broadyi* gen. nov., sp. nov., *Lucinutrix cipepodicola* gen. nov., sp. no., and novel species of the genera *Bizionia, Gelidibacter* and *Gillisia*. International Journal of Systematic and Evolutionary Microbiology, 55: 1471-1486.
5. Cipriano, R. C. and R. A. Holt. 2005. *Flavobacterium psychrophilum*, cause of Bacterial Cold-Water Disease and Rainbow Trout Fry Syndrome. Fish Disease Leaflet No. 86. United States Dept. of the Interior. U.S. Geological Service, National Fish Health Research Laboratory, Kearneysville, W. Va.
6. Handlinger, J., Soltani, M., and Percival, S. 1997. The pathology of *Flexibacter maritimus* in aquaculture species in Tasmania, Australia. J. Fish Dis. 20: 159-168.
7. Izumi, S. and Aranashi, F. 2004. Relationship between gyrA mutations and quinolone resistance in *Flavobacterium psychrophilum* isolates. Appl Environ Microbiol. 2004 July; 70(7):3968-72.
8. Karlsen, C., Sørum, H., Willassen, N. P., Åsbakk, K. 2012. *Moritella viscosa* bypasses Atlantic salmon epidermal keratocyte clearing activity and might use skin surfaces as a port of infection. Vet Microbiol, 154(3-4):353-62. Epub 2011 Jul. 30.
9. Lunder, T., Evensen, Ø., Holstad, G., and Håstein, T. 1995. "Winter ulcer" in the Atlantic salmon *Salmo salar*. Pathological and bacteriological investigations and transmission experiments. Dis. Aquat. Org. 23: 39-49.
10. Løvoll, M., Wiik-Nielsen, C. R., Tunsjø, H. S., Colquhoun, D., Lunder, T., Sørum, H., Grove, S. 2009. Atlantic salmon bath challenged with *Moritella viscosa*—Pathogen invasion and host response. Fish Shellfish Immunol, 26: 877-884.
11. Nematollahi A, Decostere A, Pasmans F, Haesebrouck F. 2003. *Flavobacterium psychrophilum* infections in salmonid fish. J Fish Dis.; 26(10):563-74.
12. Prasad et al. 2013 (Curr. Microbiol., DOI 10.1007/s00284-013-0467-6, In Press, published online Oct. 10, 2013)
13. Roar Gudding (Editor) et al. "Fish Vaccinology", Developments in Biological Standardization, 484 pages.
14. Toranzo, A. E., Magarinos, B., Romalde, J. L. 2005. A review of the main bacterial fish diseases in mariculture systems. Aquaculture 246 (2005) 37-61.
15. Torella, F. and Morita, R. Y. 1981. Microcultural study of bacterial size changes and microcolony and ultramicrocolony formation by heterotrophic bacteria in seawater. Appl. Environ Microbiol, 41: 518-527.
16. Whitman, K. A., Backman, S., Benediktsdottir, E., Coles, M. Johnson G. R. 2001. Isolation and characterization of a new *Vibrio* spp. (*Vibrio wodanis*) associated with 'winter ulcer disease' in sea water raised Atlantic salmon (*Salmo salar* L.) in New Brunswick. In C. I. Hendry & S. E. McGladdery (Eds.), Aquaculture Canada 2000 (pp. 115-117). Moncton, N B: Aquaculture Association of Canada, St. Andrews, Nebr.
17. Bjørnsdottir B, Hjerde E, Bragason B T, Gudmundsdottir T, Willassen N P, Gudmundsdottir B K. 2012. Identification of type VI secretion systems in *Moritella viscosa*. Vet Microbiol. 2012 Aug. 17; 158(3-4):436-42.

The invention claimed is:

1. A composition comprising *Bizionia* sp., wherein said *Bizionia* sp. is *Bizionia piscinecroseptica* that is inactivated by formalin.

2. The composition of claim 1, wherein said *Bizionia piscinecroseptica* is *Bizionia piscinecroseptica* 130524K2F7 deposited at National Collection of Industrial, Food and Marine Bacteria under the accession number NCIMB 42183.

3. The composition of claim 1, wherein said composition further comprises a pharmaceutically acceptable excipient and/or adjuvant.

4. The composition of claim 1, wherein said composition further comprises additional bacteria of other genera and/or species and/or strains and/or an antigen of said bacteria.

5. The composition of claim 4, wherein said additional bacteria are inactivated bacteria selected from the group consisting of *Moritella viscosa, Aliivibrio wodanis, Tenacibaculum* sp., *Tenacibaculum maritimum, Vibrio* sp., *Photobacter* sp., *Aeromonas salmonicida* subspecies, *salmonicida, Aliivibrio logei, Aliivibrio salmonicida, Flavobacterium, Flavobacterium psychrophilum, Flavobacterium columnare, Aliivibrio friggiae* and/or *Vibrio anguillarum*.

6. The composition of claim 1, wherein said composition further comprises *Aliivibrio friggiae* and/or an antigen(s) thereof, wherein the *Aliivibrio friggiae* are inactivated.

7. The composition of claim 1, wherein said composition further comprises *Aliivibrio wodanis* and/or an antigen(s) thereof, wherein the *Aliivibrio wodanis* are inactivated.

8. The composition of claim 1, wherein said composition further comprises *Aliivibrio wodanis* and/or an antigen(s) thereof, and *Allivibrio friggiae* and/or an antigen(s) thereof, wherein the *Aliivibrio friggiae* are inactivated.

9. The composition of claim 1, wherein said composition further comprises *Moritella viscosa* that are inactivated.

10. A method of immunizing fish against bizioniosis comprising the administration of a pharmaceutically effective amount of a composition comprising inactivated *Bizionia piscinecroseptica* 130524K2F7 inactivated by heat or formalin to a fish in need thereof.

11. The method according to claim 10, wherein said administration is performed by intraperitoneal injection, bath vaccination and/or by oral vaccination.

* * * * *